United States Patent
Hill et al.

(10) Patent No.: US 7,927,343 B2
(45) Date of Patent: Apr. 19, 2011

(54) METHODS, SYSTEMS, AND APPARATUS FOR PERFORMING MINIMALLY INVASIVE CORONARY ARTERY BYPASS GRAFT SURGERY

(75) Inventors: J. Donald Hill, Tiburon, CA (US); Geoffrey Briggs, Los Altos, CA (US); John Cvinar, Newton, MA (US); Andy H. Levine, Newton, MA (US); Eric May, Norfolk, MA (US); John Meade, Mendon, MA (US); Michael Sims, Montara, CA (US)

(73) Assignee: J. Donald Hill, San Francisco, CA (US)

( * ) Notice: Subject to any disclaimer, the term of this patent is extended or adjusted under 35 U.S.C. 154(b) by 803 days.

(21) Appl. No.: 10/715,826

(22) Filed: Nov. 19, 2003

(65) Prior Publication Data
US 2004/0242968 A1    Dec. 2, 2004

Related U.S. Application Data

(60) Provisional application No. 60/427,248, filed on Nov. 19, 2002.

(51) Int. Cl.
*A61B 17/08* (2006.01)
(52) U.S. Cl. ........................ 606/153; 606/151
(58) Field of Classification Search ............... 606/153, 606/213, 151, 108
See application file for complete search history.

(56) References Cited

U.S. PATENT DOCUMENTS

| | | | |
|---|---|---|---|
| 58,957 A | 5/1902 | Farascioni | |
| 91,300 A | 7/1902 | Peng et al. | |
| 3,254,650 A | 6/1966 | Collito | |
| 4,366,819 A * | 1/1983 | Kaster | 606/153 |
| 4,573,452 A | 3/1986 | Greenberg | |
| 4,817,587 A | 4/1989 | Janese | |
| 5,456,714 A * | 10/1995 | Owen | 623/1.31 |
| 5,824,061 A * | 10/1998 | Quijano et al. | 623/1.13 |
| 5,904,697 A * | 5/1999 | Gifford et al. | 606/155 |
| 6,074,416 A | 6/2000 | Berg et al. | |
| 6,142,935 A | 11/2000 | Flom et al. | |
| 6,190,311 B1 | 2/2001 | Glines et al. | |

(Continued)

FOREIGN PATENT DOCUMENTS

WO    WO 9840036    9/1998
(Continued)

*Primary Examiner* — Darwin P Erezo
(74) *Attorney, Agent, or Firm* — Baker Botts L.L.P.

(57) ABSTRACT

A system for performing vascular surgery includes a first retractor blade and a second retractor blade and a fulcrum device. The first retractor blade includes a first grasping bar, and the second retractor blade comprises a second grasping bar. The first retractor blade and the second retractor blade are adapted to engage opposing edges of a subcostal incision in a patient. The fulcrum device includes a first fulcrum slot and a second fulcrum slot formed through opposing edges of the fulcrum device. The first fulcrum slot is adapted to receive the first grasping bar and the second fulcrum slot is adapted to receive the second grasping bar, such that the fulcrum device is adapted to apply leverage from the first retractor blade and the second retractor blade to spread the edges of the incision and to allow access to a chest cavity of the patient.

13 Claims, 43 Drawing Sheets

U.S. PATENT DOCUMENTS

| | | |
|---|---|---|
| 6,371,965 B2 | 4/2002 | Gifford, III et al. |
| 6,395,015 B1 * | 5/2002 | Borst et al. .................... 606/213 |
| 6,524,322 B1 * | 2/2003 | Berreklouw .................. 606/153 |
| 6,814,750 B2 * | 11/2004 | Kavteladze et al. ......... 623/1.22 |
| 2001/0001122 A1 | 5/2001 | Gifford et al. |
| 2001/0049549 A1 * | 12/2001 | Boylan et al. ................. 623/1.11 |
| 2002/0116018 A1 * | 8/2002 | Stevens et al. ............... 606/153 |
| 2002/0151914 A1 * | 10/2002 | Gifford et al. ................ 606/153 |
| 2002/0161383 A1 * | 10/2002 | Akin et al. .................... 606/153 |
| 2003/0088256 A1 * | 5/2003 | Conston et al. .............. 606/155 |
| 2004/0087984 A1 * | 5/2004 | Kupiecki et al. ............. 606/153 |
| 2005/0192604 A1 * | 9/2005 | Carson et al. ................ 606/153 |

FOREIGN PATENT DOCUMENTS

| | | |
|---|---|---|
| WO | WO 9840036 A1 * | 9/1998 |
| WO | WO 0024339 | 5/2000 |
| WO | WO 0024339 A * | 5/2000 |
| WO | WO 0072764 | 12/2000 |
| WO | WO 0141633 | 6/2001 |
| WO | WO 0141653 | 6/2001 |
| WO | WO 0178801 | 10/2001 |
| WO | WO 02058591 | 8/2002 |

* cited by examiner

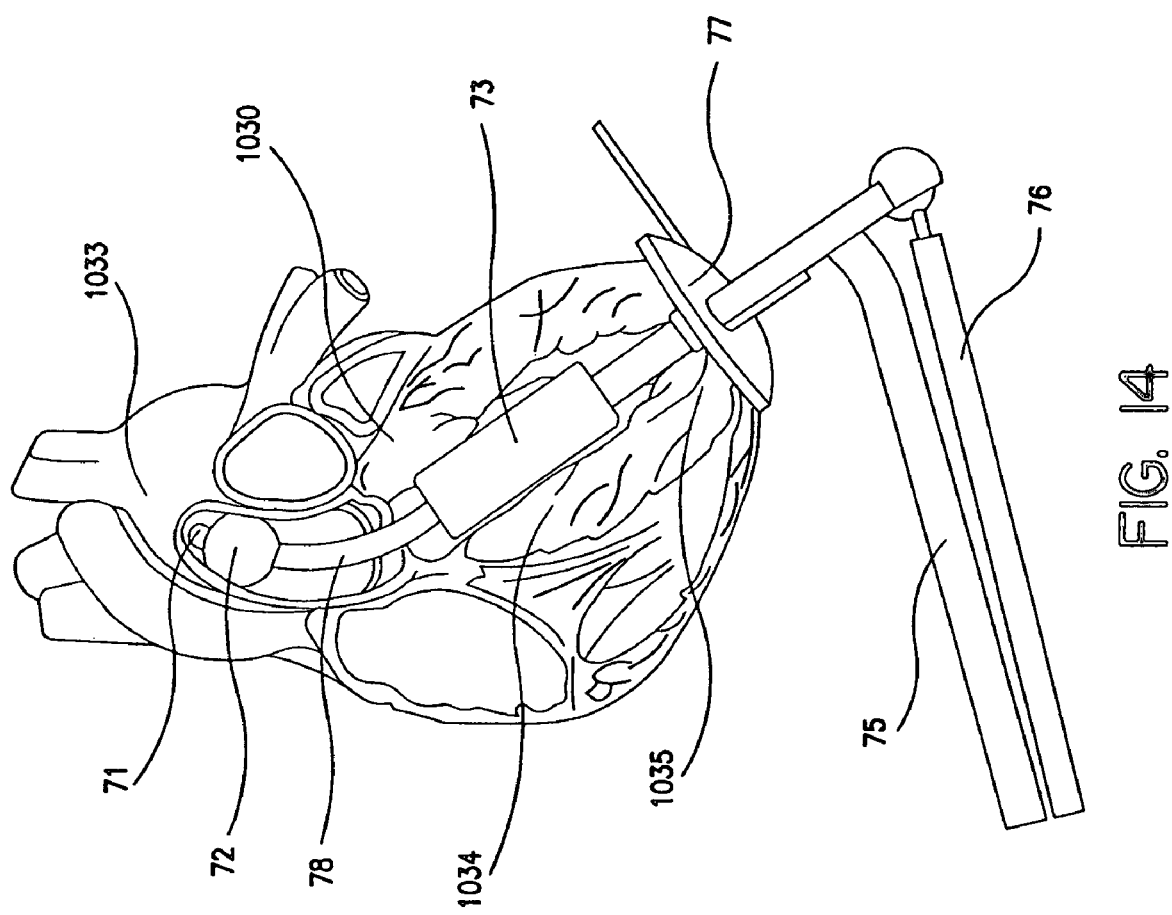

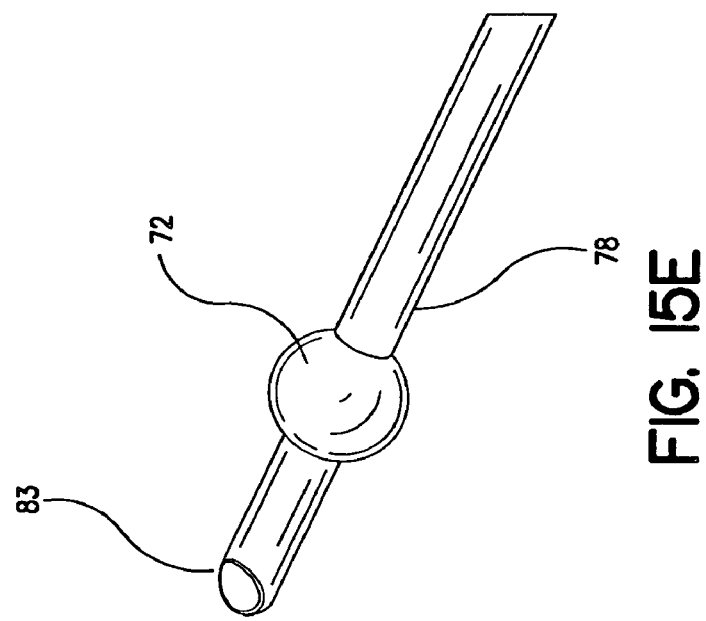
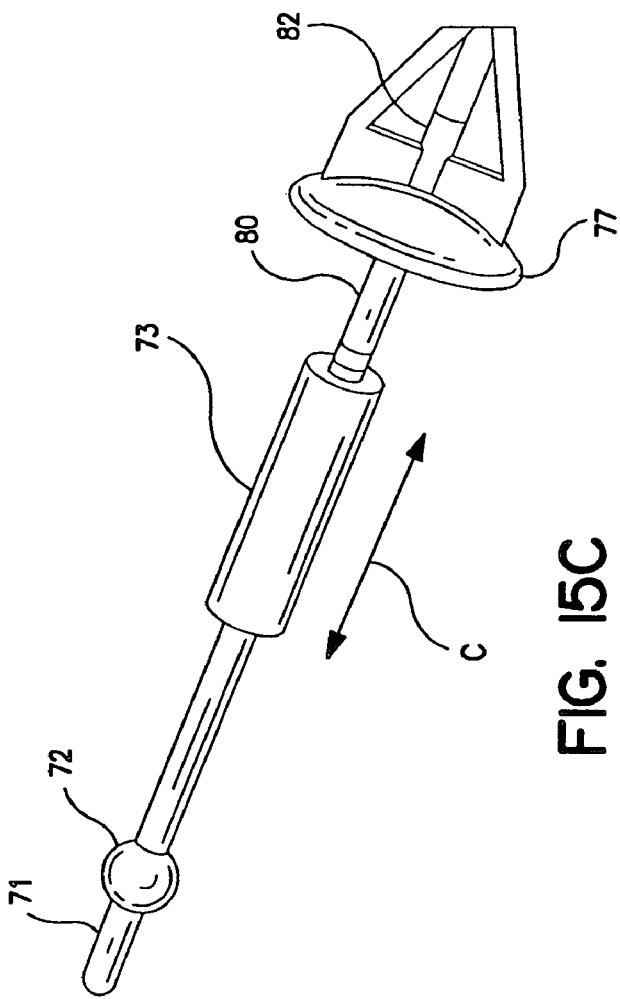
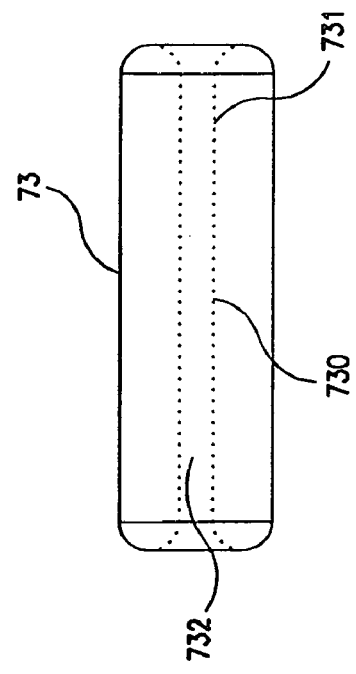

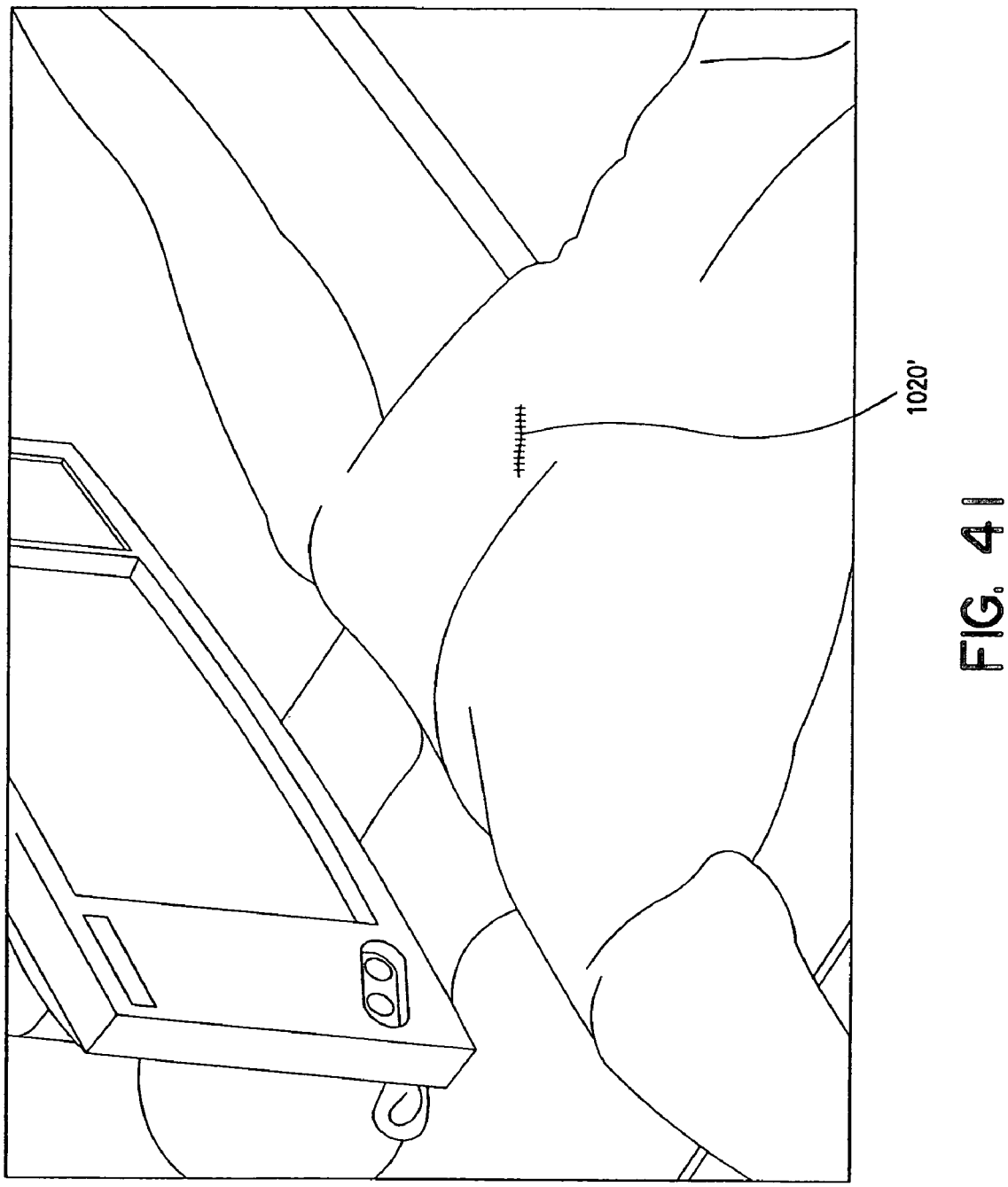

METHODS, SYSTEMS, AND APPARATUS FOR PERFORMING MINIMALLY INVASIVE CORONARY ARTERY BYPASS GRAFT SURGERY

This application claims the benefit of U.S. Provisional Patent Application No. 60/427,248, filed Nov. 19, 2002, which is incorporated herein by reference.

BACKGROUND OF THE INVENTION

1. Field of the Invention

This invention relates to the field of less or minimally invasive surgery for the purposes of revascularizing tissue. In particular, the invention relates to methods, systems, and apparatus for performing less or minimally invasive, Coronary Artery Bypass Grafting (CABG) surgery for the purposes of revascularizing tissue. Still more particularly, such systems and methods may employ conduit coupling devices. Specifically, conduit coupling devices may be used which are formed from couplers to connect conduits, such as arteries, veins, or the like, and to establish fluid communication therebetween and methods for establishing such fluid communication using such coupling devices.

2. Description of Related Art

Arteries supply tissue with nutrients and oxygen carried by blood. When arteries become diseased or obstructed, the delivery of blood to tissue may be compromised. When the tissue is denied such nutrients and oxygen, the tissue becomes ischemic and necrotic. Healthy arteries and veins may be harvested from other parts of the body and connected to diseased or obstructed vessels to bypass the diseased or obstructed portions and to restore delivery of blood to tissue, thereby reducing or preventing further tissue damage or loss. Once completed, the bypass may deliver blood flow to tissue distal to the obstruction, thereby reducing or preventing further tissue loss. When such procedures are performed on the heart, such procedures have been called CABG surgery.

Known CABG surgery methods have been performed for years by stopping the heart, placing the patient on Cardiopulmonary Bypass (CPB) apparatus, and opening the chest cavity by cutting through the ribs at the sternum. Bypass vessels then may be attached to the diseased arteries by tedious and time-consuming suturing techniques. Although the surgeon may gain the least obstructed access to the patient's heart through the ribs, i.e., by "cracking" the patient's chest, the patient's recovery may be delayed and the risk of infection and other complications associated with heart surgery may increase with such invasive techniques. Bypass suturing of this type is performed using a surgical procedure in which the chest wall remains open, thereby exposing the heart. Because such bypass procedures may be time-consuming, a patient may be subjected to prolonged anesthesia and to the use of a CPB or other cardiopulmonary support system. Prolonged exposure of a patient to these conditions may increase the likelihood of adverse reactions including delayed recover or loss of mental faculty, stroke, or death.

As noted above, known surgical bypass techniques may involve the harvesting of a blood vessel from the chest wall or the leg of a patient for use as a bypass conduit. The bypass procedure involves extensive preparation of the bypass vessels; careful positioning of the bypass vessels at the bypass site; and meticulous suturing. The reduced size of sutures used may require the surgeon to use of optical magnification. Such bypass procedures are technically challenging with results highly dependent upon the skill of the surgeon. If the attachment point between the bypass vessel and the obstructed or diseased vessel is not aligned properly, a disturbance of the blood flow may occur, resulting in a reduction in the size of the opening between the vessels. Eventually, in such cases, the bypass opening may close, thereby further obstructing a flow of blood to tissue.

One way to reduce the time during which a patient is subjected to anesthesia and CPB or other support systems has been to develop less invasive approaches to cardiac surgery. Recently, attempts have been made to develop less invasive surgical techniques, but these techniques have met with only limited success. While the use of less invasive procedures employing access devices called "ports" has been attempted, thus far, this approach has achieved limited acceptance due to difficulties that may arise when suturing bypass vessels from a remote location through such ports.

SUMMARY OF THE INVENTION

A need has arisen for improved surgical methods, systems, and apparatus for performing less or minimally invasive surgeries and, in particular, less or minimally invasive CABG surgeries. It is a technical advantage of such surgical methods, systems, and apparatus that the surgeon may make a smaller incision in the patient's chest and that it is not necessary to cut through the patient's ribs. It is a further technical advantage that of such surgical methods, systems, and apparatus that they may employ or comprise a fulcrum device to hold the incision open during the surgery or a holder for surgical instruments, which may free a surgeon's hand during surgery, or both. It is still a further technical advantage that of such surgical methods, systems, and apparatus that they may employ or comprise a cannula, which combines the functions of a heart manipulation device and a catheter, to provide cardiopulmonary bypass and to deliver cardioplegia solution within the confines of the substantially closed chest cavity.

A need also has arisen for a conduit coupling device that may be introduced and positioned through a port in a patient's body, thereby eliminating the need for more invasive surgical procedures that involve opening the chest wall and thereby reducing operative time during which a patient may be subjected to anesthesia and cardiopulmonary support. A further need has arisen for a conduit coupling device that may be attached without the need for fine suturing techniques by a surgeon. A still further need has arisen for a conduit coupling device comprising a pair of couplers that may be positioned in adjacent or nearby conduits to bypass obstructed or diseased portions.

It is an advantage of such methods, systems, and apparatus that the surgeon need not open the chest cavity to gain access to the heart through the ribs, thereby reducing or minimizing trauma to the patient and speeding recovery. It is a further advantage of such methods, systems, and apparatus that the surgeon may place the patient on CPB or other cardiopulmonary support systems in order to allow manipulations of the heart that are needed to access the coronary arteries on the left side of the heart, and also to decompress the heart to provide room in the chest for instrument access. It is still a further advantage of such methods, systems, and apparatus that the vessels used to bypass diseased vessels may be reattached to the diseased vessels with unique anastomosis conduit coupling devices that eliminate the need for suturing.

A conduit coupling device according to this invention permits the attachment of blood vessels, such as arteries or veins, to obstructed or diseased arteries to bypass the obstructed or diseased portion. One advantage of the device is the ease and speed of attachment of couplers to conduits, eliminating a need for fine suturing techniques. The conduit coupling device of the present invention also improves the consistency and quality of the anastomotic procedure, which is less dependent upon surgical technique than known bypass suturing techniques. By eliminating suturing, this device and method may be performed using ports and similar surgical techniques that are less invasive. Thus, consistency of the conduit opening and flow path are less dependent upon the suturing ability of a surgeon. Use of the devices and methods disclosed herein may reduce operation time and risks associated with CABG surgery compared to known bypass devices and methods. Each coupler of a conduit coupling device according to the present invention provides a smooth, hemodynamic opening and establishes a fluid flow path between conduits being connected by the conduit coupling device.

According to an embodiment of the invention, a coupler comprises a saddle, a channel, a tissue clamp, and a flange. The channel has a first end having a substantially elliptical cross-section connected to the saddle and a second end having a substantially circular cross-section. The tissue clamp is positioned around the channel. The flange is formed adjacent to the second end of the channel. A conduit coupling device may be formed by securing flanges of two couplers together.

According to another embodiment of the invention, a method of connecting two conduits comprises the following steps. A first saddle of a first coupler is positioned within a first conduit. A second saddle of a second coupler is positioned within a second conduit. The first conduit is clamped to the first saddle of the first coupler. The second conduit is clamped to the second saddle of the second coupler. The first coupler and the second coupler are connected.

According to a further embodiment of the invention, a conduit coupling device comprises a first coupler, a second coupler, and a clamping ring. The first coupler comprises a first saddle, a first channel, a first tissue clamp, and a first flange. The second coupler comprises a second saddle, a second channel, a second tissue clamp, and a second flange. The clamping ring secures the first flange and the second flange together. The first and second couplers may be joined together at different angles relative to one another, depending upon the orientation of the conduits to be connected by the conduit coupling device.

According to still a further embodiment, the invention is a coupler holder and delivery device for holding and delivering a coupler to a blood vessel. The coupler comprises a saddle; a channel, wherein the channel comprises a first end connected to the saddle and a second end, a tissue clamp positioned around the channel; and a flange formed adjacent to the second end of the channel. The coupler holder and delivery device comprises an outer tube surrounding an inner shaft, such that the outer tube is slidable on the inner shaft and independently of the inner shaft; a coupler conforming end, which is mounted on a first end of the inner shaft and is adapted to engage the second end of the channel of the coupler; and a pair of opposing, tissue clamp receiving flanges mounted on opposite sides of a first end of the outer tube and adapted to engage the tissue clamp bend the tissue clamp away from the saddle. The outer tube is slidable toward the first end of the inner shaft to engage the flanges to the tissue clamp. Conversely, the outer tube is slidable away from the first end of the inner shaft to release the tissue clamp from the flanges.

According to yet a further embodiment, the invention is a method for delivering a coupler into a blood vessel. The coupler comprises a saddle; a channel, wherein the channel comprises a first end connected to the saddle and a second end; a tissue clamp positioned around the channel; and a flange formed adjacent to the second end of the channel. The method comprising the steps of engaging the channel of the coupler; engaging the tissue clamp and bending the tissue clamp away from the saddle; making an incision into the blood vessel; delivering the coupler into the blood vessel through the incision; securing the saddle to the blood vessel; and releasing the tissue clamp, so that the tissue clamp conforms to the saddle.

In another embodiment, the invention is a system for performing vascular surgery. The system comprises a first retractor blade and a second retractor blade, wherein the first retractor blade comprises a first grasping bar and the second retractor blade comprises a second grasping bar and wherein the first retractor blade and the second retractor blade are adapted to engage opposing edges of an incision, e.g., a subcostal incision, in a patient. The system further comprises a fulcrum device. The fulcrum device comprises a first fulcrum slot and a second fulcrum slot formed through opposing edges of the fulcrum device, wherein the first fulcrum slot is adapted to receive the first grasping bar and the second fulcrum slot is adapted to receive the second grasping bar, such that the fulcrum device is adapted to apply leverage from the first retractor blade and the second retractor blade to spread the edges of the incision and to allow access to a chest cavity of the patient.

The system further may comprise a first bar and a first mounting bracket and a second bar and a second mounting bracket. The first retractor blade is mounted adjustably, e.g., slidably, and pivotably on the first bar by the first mounting bracket and the second retractor blade is mounted adjustably, e.g., slidably, and pivotably on the second bar by the second mounting bracket. In this manner, a separation between the first retractor blade and the second retractor blade is adjustable to increase or decrease the separation between the edges of the incision in the patient.

The system further may comprise a surgical table comprising a central support for supporting the patient's head and trunk, a pair of arm supports extending from opposing edges of the central support, and a pair of leg supports for supporting and separating the patient's legs. In this manner, an angle of separation between the patient's legs is adjustable to permit improved access to the patient's chest by a surgeon standing between the patient's legs.

The system further may comprise a first bar and a first mounting bracket and a second bar and a second mounting bracket. The first retractor blade is mounted adjustably, e.g., slidably, and pivotably on the first bar by the first mounting bracket and the second retractor blade is mounted adjustably, e.g., slidably, and pivotably on the second bar by the second mounting bracket. The first bar and the second bar also may be mounted on the surgical table. In this manner, a separation between the first retractor blade and the second retractor blade is adjustable.

The fulcrum device of this system may comprise a perimeter lip having an access opening, e.g., a window-like opening, formed therewithin, a pair of parallel first rails which extend across the access opening, and an instrument support slidably mounted between the pair of parallel first rails, such that the instrument support holds a surgical instrument inserted into the patient's chest cavity. The instrument support further may comprise a pair of first grasping runners, which slidably engage the pair of parallel first rails; a pair of parallel second rails which extend between the pair of first grasping runners; and an instrument port slidably mounted between the pair of parallel second rails. In this manner, the instrument port is positionable within the access opening along a first axis parallel to the pair of parallel first rails and along a second axis parallel to the pair of parallel second rails and perpendicular to the first axis. The instrument port further may comprise a pair of second grasping runners, which slidably engage the pair of parallel second rails, and an instrument access orifice formed therethrough. The instrument access orifice may receives a surgical instrument and hold it at a position within the access opening. Other instruments may be manipulated directly through the access opening. The fulcrum device also may comprise a light source to illuminate the chest cavity. The light source may comprise a plurality of light emitting diodes (LEDs) arrayed about a side of the perimeter lip facing the patient's chest cavity. In yet another embodiment, the light source may comprise at least one fiber optic cable to convey light to a plurality of fiber optic cable ends arrayed about a side of the perimeter lip facing the patient's chest cavity.

A variety of instruments may be used in this system and manipulated through the fulcrum devices access opening. An endoscope and an endoscope holding device, wherein the endoscope holding device may comprise a first ball joint, a second ball joint, and a manipulating shaft extending between the first ball joint and the second ball joint; an endoscope stabilizing device supporting the second ball joint, whereby the endoscope holding device is fixed to a stationary object; a handle mounted on the first ball joint comprising a passage formed therethrough for receiving the endoscope and a activating lever. The first ball joint and the second ball joint are thereby released and secured.

A dissecting instrument for separating tissue may comprise a handle, a shaft, and a tip, wherein the shaft is rotatable and the tip is rotatable and pivotable on the shaft. The tip further may comprise dissecting means. The dissecting means may comprises a spatula end affixed to a spatula end shaft and a grasper jaw affixed to the spatula end shaft, such that the grasper jaw is brought into contact with the spatula end to blunt dissect tissue positioned therebetween. A first button mounted on the handle may be manipulated to pivot the tip via mechanical couplings within the shaft, and a second button mounted on the handle may be manipulated to actuate the grasper jaw via mechanical couplings within the shaft. In another embodiment, the dissecting means comprises a source of $CO_2$ and a gas flow passage for conveying $CO_2$ to the tip. In this manner, a flow of $CO_2$ separates impacted tissue into natural tissue planes prior to dissection. In still another embodiment, the dissecting means may comprise a source of RF energy and a conduit for conveying RF energy to an innermost surface of spatula end shaft. In this embodiment, the second button mounted on the handle is manipulated to actuate the grasper jaw via mechanical couplings within the shaft to seize tissue to coagulate blood in the tissue prior to dissection. Alternatively, the dissecting means may include a combination of some or all of these embodiments.

A cannula for use in this system may comprise a stabilizer and manipulation component and a catheter component. The stabilizer and manipulation component may be adapted to receive the catheter component and may comprise a suction cup adapted to secure the stabilizer and manipulation component to an apex of the patient's heart; a suction tube through which fluid is drawn to create suction between the suction cup and the heart; a stabilizer shaft which passes through the suction cup and is adapted to penetrate the heart through an incision; a hemostatic valve in communication with the stabilizer shaft for insertion of the catheter component into the heart; and a manipulator arm and handle for guiding the suction cup into contact with the heart. The catheter component may be adapted to be received by the stabilizer and manipulation component and may comprise at least one catheter tube adapted to pass through the stabilizer and manipulation component in to the patient's heart; a proximal balloon, which deploys radially in the left ventricle; a distal balloon that deploys radially in the ascending aorta, at least one radial discharge opening formed in the at least one catheter tube between the distal balloon and the proximal balloon; and a distal discharge opening formed at the tip of the at least one catheter tube.

Tissue scissors may comprise a scissors handle, a scissors shaft, a distal end pivotable on the scissors shaft at a distal end joint; a slidable button mounted on the scissors handle and operably connected to the distal end joint, whereby the distal end is pivoted; a pair of scissor blades mounted on the distal end; and a handle ring operably connected to at least one of the pair of scissor blades, whereby at least one of the pair of scissor blades in urged into contact with the other of the pair of scissor blades. Such tissue scissors further may comprise a source of RF energy and a conduit for conveying RF energy to at least one of the pair of scissor blades.

Yet another instrument for use in this system, is a coupler connection device for connecting a pair of couplers to each other. Such a coupler connection device may comprise a connection shaft, a pair of coupler connecting arms, and a connecting pivot; wherein each of the coupler connecting arms further comprises a pair of arched fingers positioned at the end of the coupler connecting arm opposite the connecting pivot, which grasp one of the pair of couplers, and wherein at least one of the pair of coupler connecting arms pivots on the connecting pivot towards the other of the pair of coupler connecting arms to connect the couplers to each other.

In still yet a further embodiment, this invention is a method of performing vascular surgery. This method may comprise the steps of: making a subcostal incision in a patient; engaging opposing edges of the incision with a first retractor blade and a second retractor blade; mounting a fulcrum device on the first retractor blade and the second retractor blade; retracting the incision to provide access to the patient's chest cavity through which to operate; placing a heart blade through the fulcrum device; inserting an endoscope through the fulcrum device to locate damage in a coronary vessel; positioning the heart with the heart blade to expose the damaged coronary vessel and a branch of the Internal Mammary Artery (IMA); inserting a cannula through the fulcrum device into the apex of the patient's heart to place the patient on cardiopulmonary bypass; making a vessel incision in the coronary vessel downstream from the located damage in the coronary vessel and inserting a first conduit coupler into the vessel incision; making an IMA incision in the IMA and inserting a second conduit coupler into the IMA incision; connecting the first conduit coupler to the second conduit coupler; removing the cannula from the patients heart; and supplying blood to tissue downstream of the located damage via the first conduit coupler and the second conduit coupler.

Other objects, features and advantages will be apparent to persons skilled in the art from the following detailed description of the invention and the accompanying drawings.

BRIEF DESCRIPTION OF THE DRAWINGS

The invention may be understood more readily by reference to the following drawings.

FIG. 14 depicts the positioning of the cannula in the heart.

FIG. 15C depicts the portion of cannula between the cannula tip and the suction cup with both cannula balloons inflated. FIG. 15D shows a cross-sectional view of the proximal balloon of FIG. 15C. FIG. 15E depicts the cannula tip and the distal balloon and indicates the relative positions of the distal and radial discharge openings.

FIG. 41 depicts the final wound on the patient.

DETAILED DESCRIPTION OF THE DRAWINGS

Patient Positioning

Figure 1:
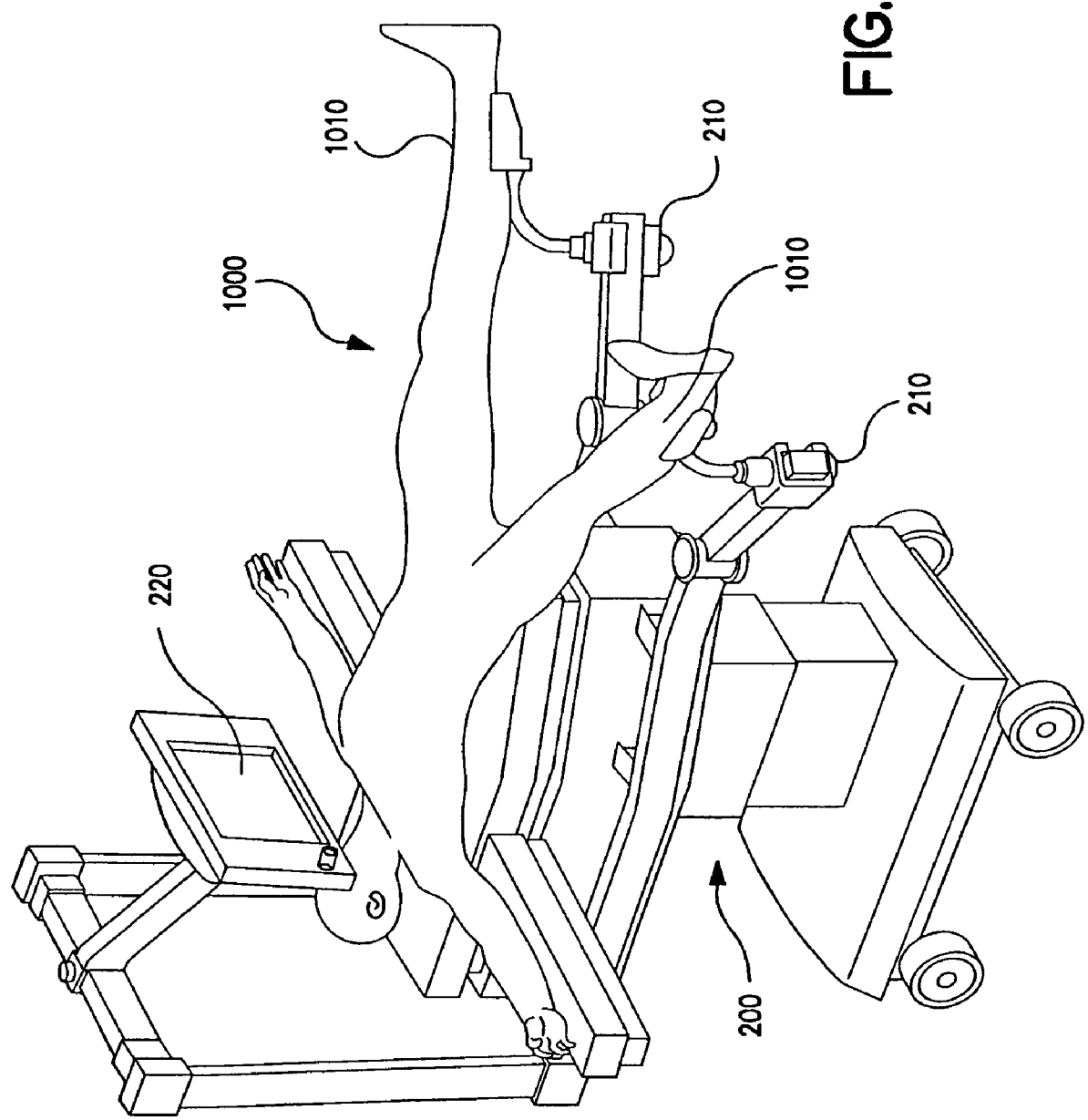
FIG. 1 depicts a surgical table and the positioning of a patient on such a surgical table.
Figure 2:
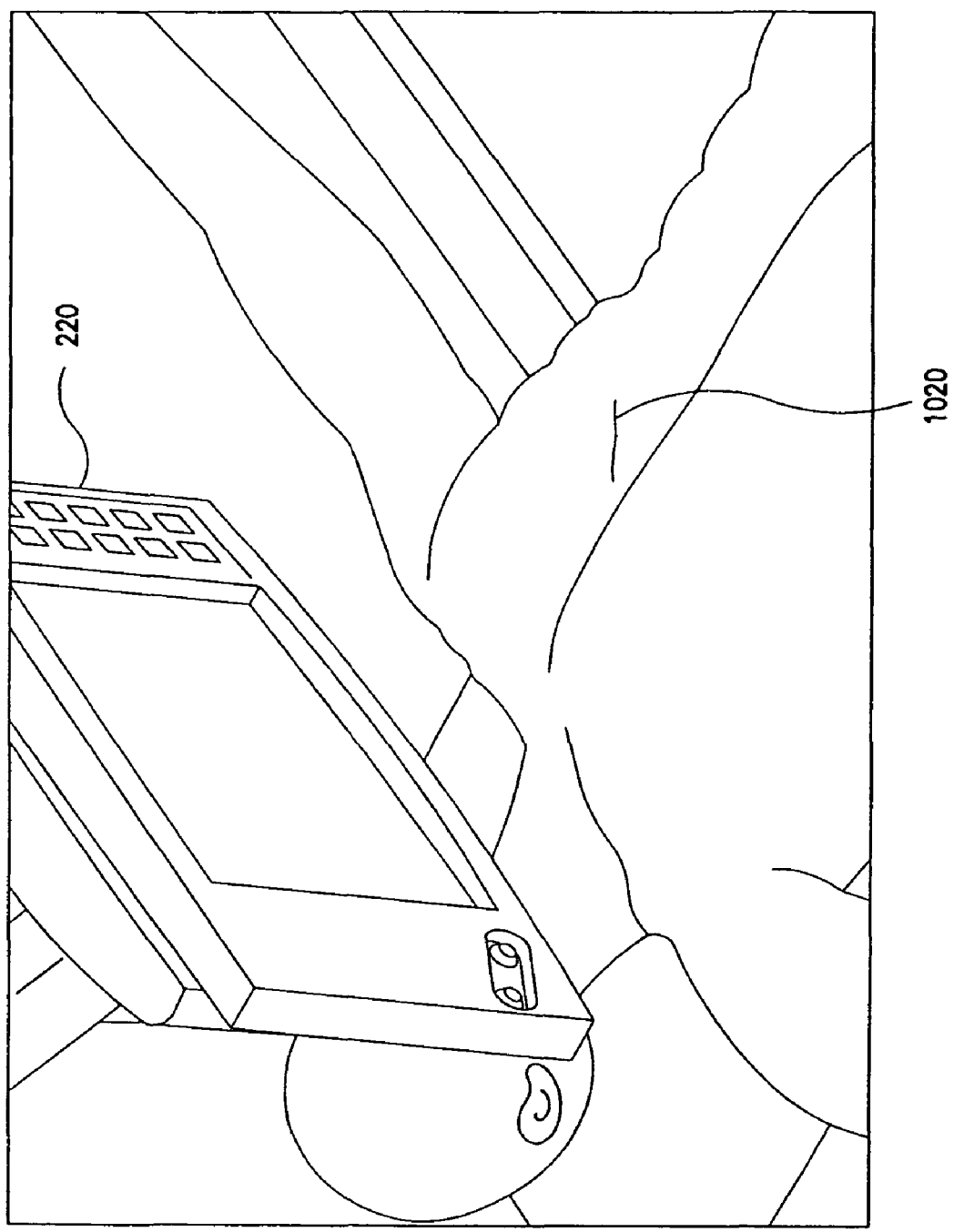
FIG. 2 depicts the sub-costal incision into the patient's chest to the left of the midline.

A patient 1000 is positioned on the a surgical table 200, as shown in FIG. 1. The surgeon (not shown) stands between the legs 1010 of patient 1000. Patient's legs 1010 are spread apart and rest on a pair of supports 210. A sub-costal incision 1020, as shown in FIG. 2, is made below the ribs on the left side of patient 1000 and extends for about six centimeters from the midline of patient 1000 outwards. The surgical table also may comprise a video monitor 200 and a camera (not shown), whereby images of the patient's chest cavity are displayed on the video monitor. Video monitor 220 is positioned just above patient 1000 for ready viewing by the surgeon.

Incision Retraction

Figure 3:
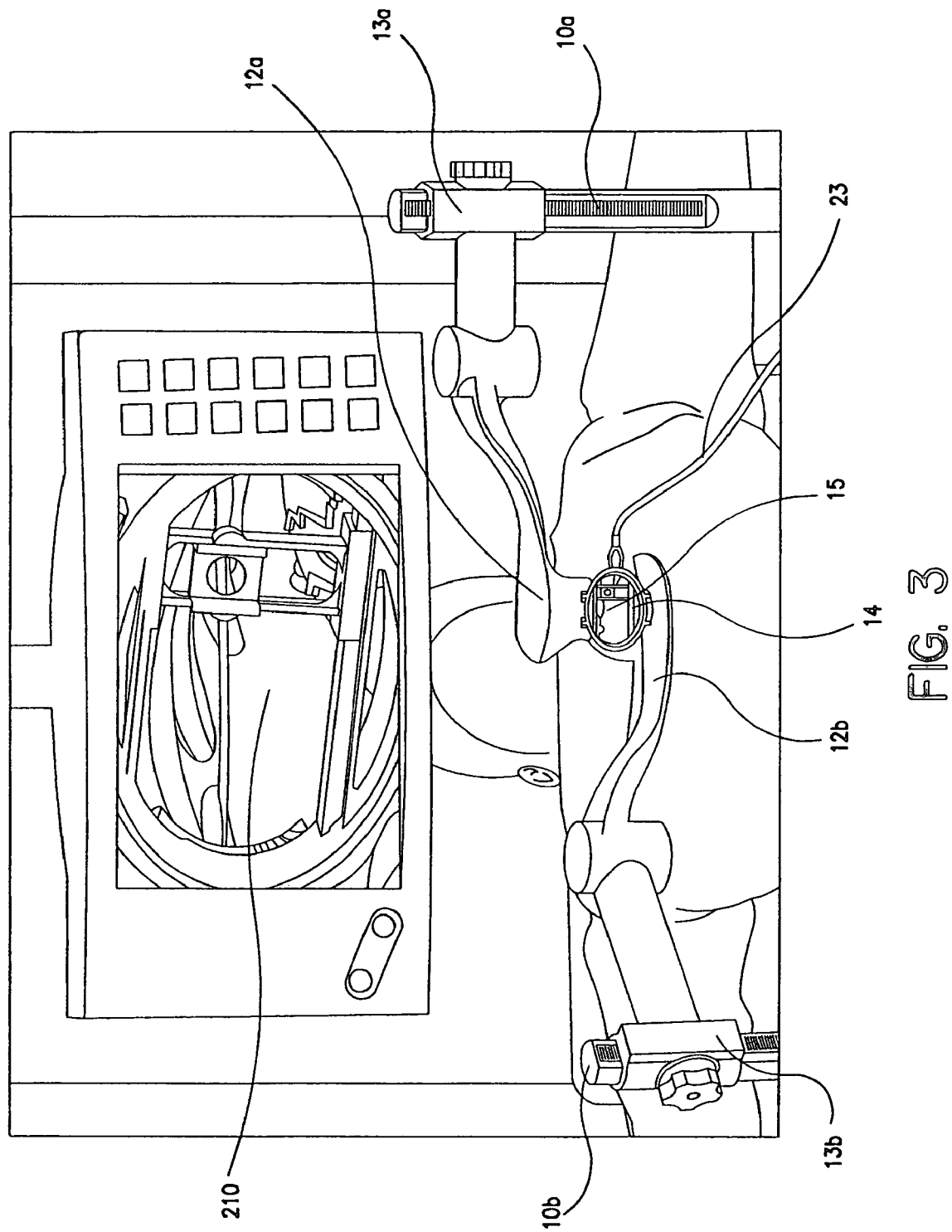
FIG. 3 depicts retraction of the incision with the retractors and a fulcrum device in place.
Figure 4:
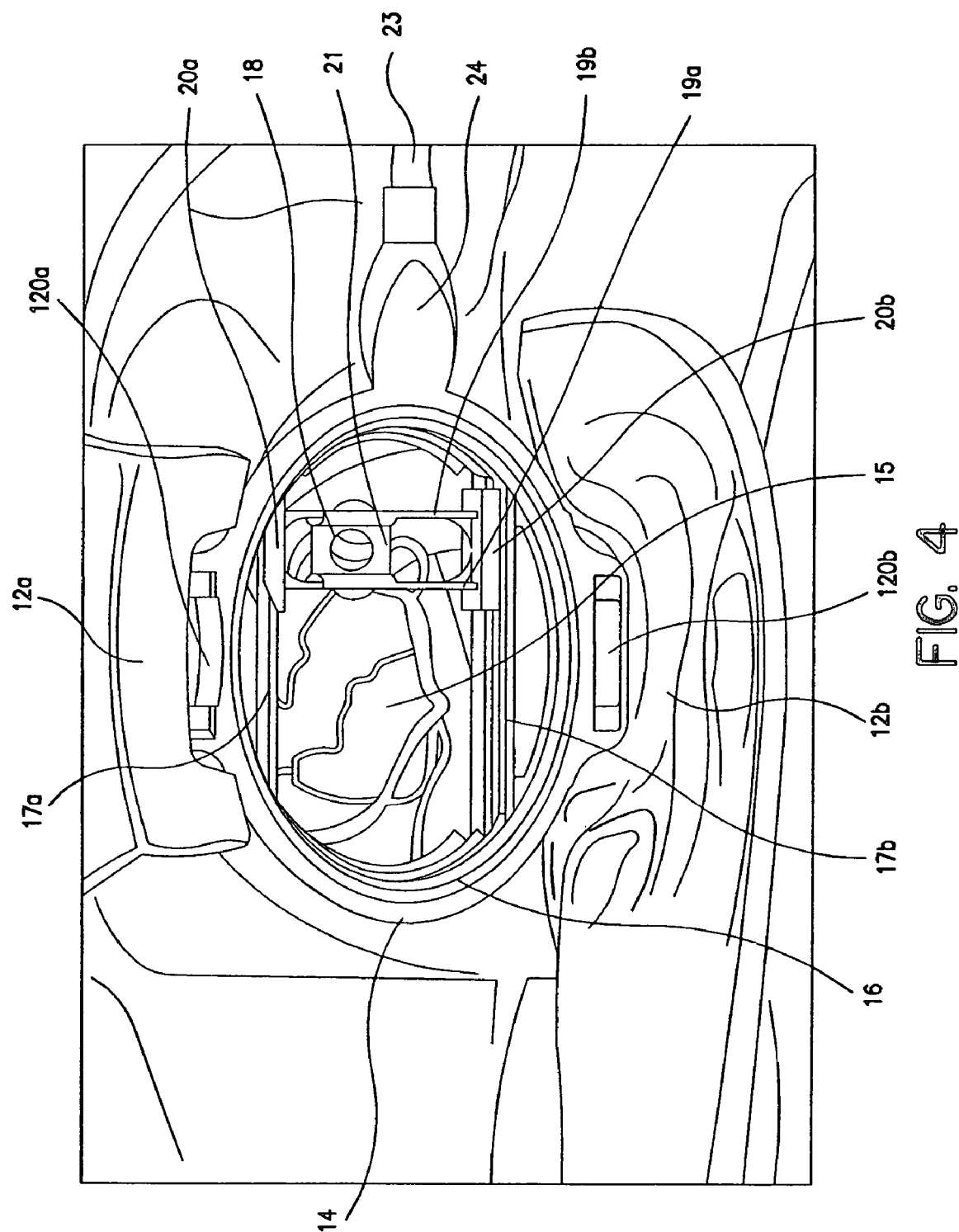
FIG. 4 depicts a close view through the fulcrum device and into the retracted incision.
Figure 5:
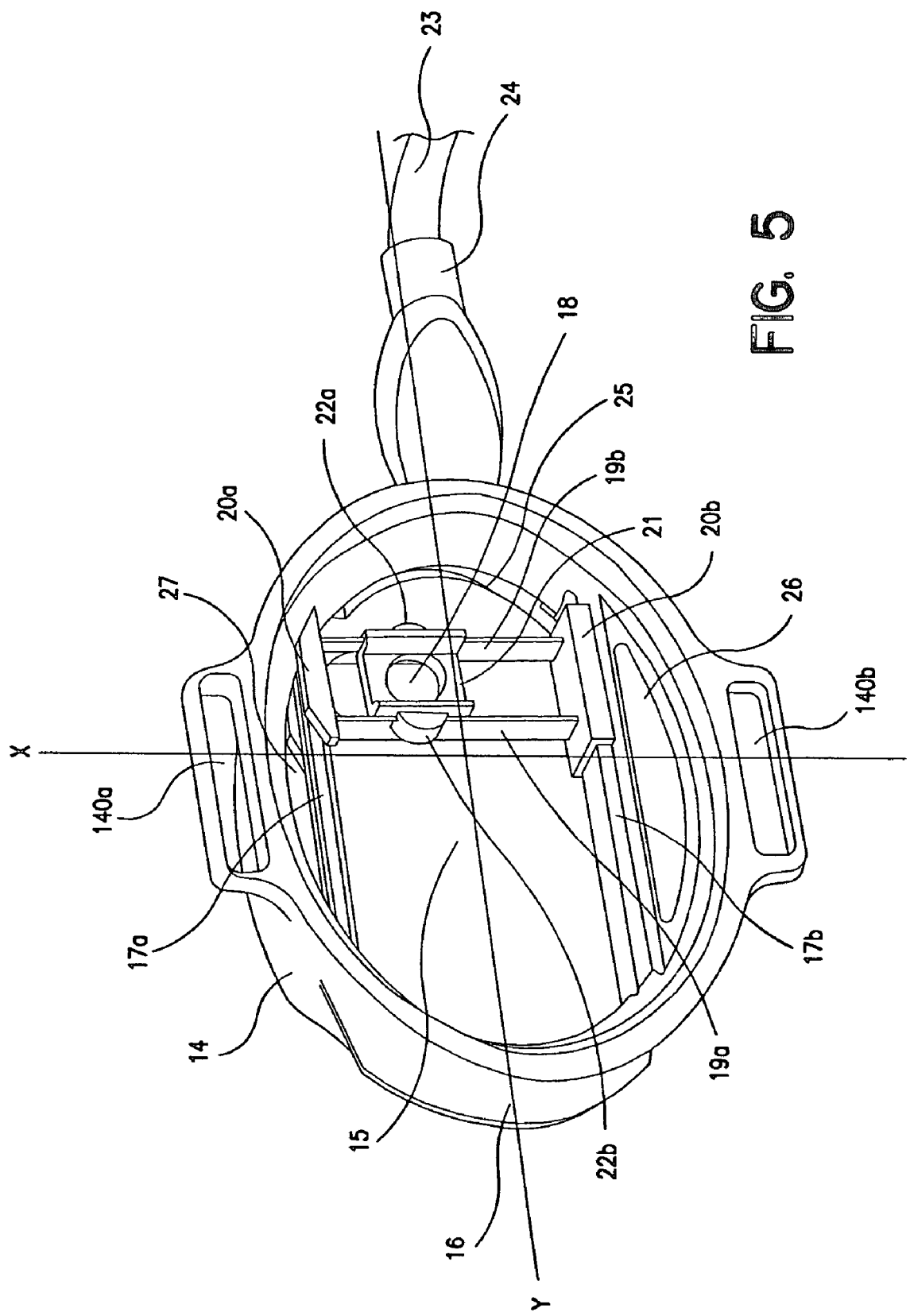
FIG. 5 depicts the fulcrum device.

Incision 1020 then is opened, e.g., spread or separated, as shown in FIG. 3, by means of two retractor blades 12a and 12b. Upper retractor blade 12a connects to a vertical bar 10a, which is attached to surgical table 200. A first mounting bracket 13a permits vertical movement of upper retractor blade 12a to increase or decrease the blade retraction. Similarly, lower retractor blade 12b attaches through a second vertical bar 10b to surgical table 200 through a second mounting bracket 13b. Second mounting bracket 13b also permits vertical movement of lower retractor blade 12b to increase or decrease the blade retraction. Retractor blades 12a and 12b engage a fulcrum device 14, as shown in FIG. 4. Fulcrum device 14 may be sized to correspond to the size of incision 1020 and is placed into incision 1020 to maintain a window-like opening 15 to the patient's chest. Upper retractor blade 12a passes through upper fulcrum slot 140a and lower retractor blade 12b passes through lower fulcrum slot 140b. Referring to FIG. 5, upper retractor blade 12a is equipped with an upper grasping bare 120a to engage upper fulcrum slot 140a, lower retractor blade 12b is equipped with a lower grasping bar 120b to engage lower fulcrum slot 140b.

Fulcrum Device

Fulcrum device 14 in FIGS. 4 and 5 contains a perimeter lip 16 that runs around fulcrum device 14 and, in an embodiment of the invention, may give fulcrum device 14 a substantially elliptical shape. The tissue on either side of incision 1020 is captured in perimeter lip 16. Fulcrum device 14 has two parallel, first rails 17a and 17b, which extend across window-like opening 15. An instrument support 18 comprises two parallel, second rails 19a and 19b; a pair of first grasping runners 20a and 20b, to which the ends of second rails 19a and 19b are joined; and an instrument port 21 having an instrument access orifice formed therethrough and a pair of second grasping runners 22a and 22b which slidably engage second rails 19a and 19b. Surgical instruments, such as those described herein, may be passed through the instrument access orifice and into the patient's chest. First grasping runners 20*a* and 20*b* slidably engage first rails 17*a* and 17*b*, respectively, so that instrument support 18 may be moved perpendicular to a first axis X of fulcrum device 14. Similarly, second grasping runners 22*a* and 22*b* slidably engage second rails 19*a* and 19*b*, respectively, so that instrument port 21 may be moved perpendicular to a second axis Y of fulcrum device 14. Thus, instrument port 21 may be positioned at almost any location within window-like opening 15. Second rails 19*a* and 19*b* may be joined to first grasping runners 20*a* and 20*b* or formed integrally with first grasping runners 20*a* and 20*b* to form instrument support 18.

Second grasping runners 22*a* and 22*b* may operate when squeezed towards each other to release instrument port 21 to move vertically on the second rails 19*a* and 19*b*. Friction may keep instrument support 18 from moving laterally along the first rails 17*a* and 17*b*.

Fulcrum device 14 also may comprise a light transmitting cord 23, such as a fiber optic cable or cables, which is attached to a light source (not shown). Cord 23 is connected to fulcrum device 14 through connector 24. Light transmitted by cord 23 and is supplied to one or more emitters 25, which emitters 25 may be arrayed around the side of fulcrum device 14 facing the patient's chest cavity. Thus, emitters 25 may supply sufficient light inside the chest cavity for visualization of the surgical site or sites by the surgeon or by a camera for transmission to and display on monitor 220. For example, emitters 25 may be the ends of fiber optic cables. In another embodiment of the invention, however, cord 23 and connector 24 may be replaced with a power cable and emitters 25 may be light emitting diodes (LEDs) or other light emitting electrical or electronic devices.

Heart Blade

Figure 6:
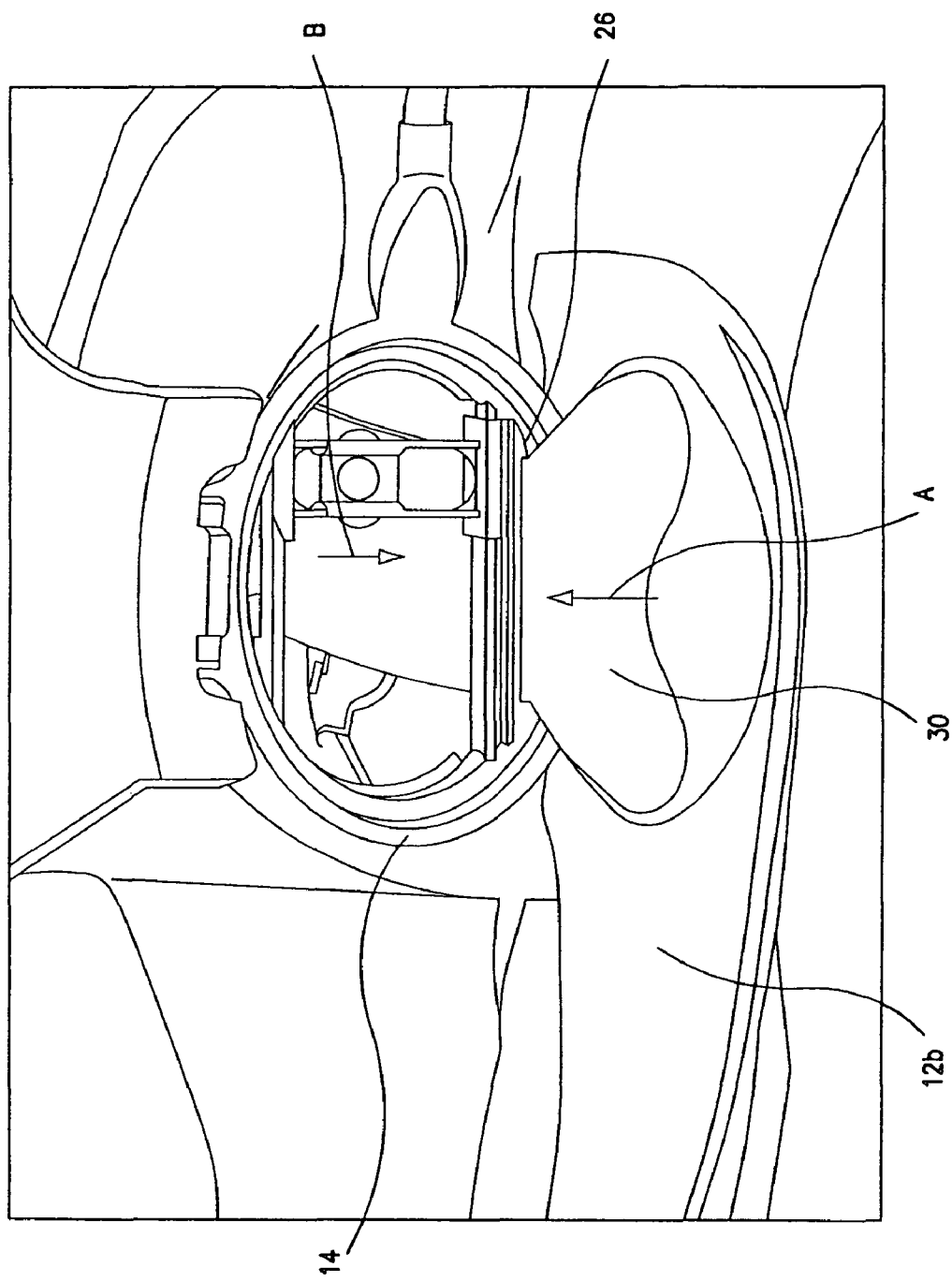
FIG. 6 is a view inside the chest through the fulcrum device with the heart blade in place.

Referring to FIG. 6, a heart blade 30 may be passed through lower fulcrum passage 26 in fulcrum device 14. Heart blade 30 may be used position the patient's heart, e.g., to push the heart down, while the surgeon operates inside the patient's chest cavity. This use of heart blade 30 may provide more space within the cavity. By pulling upward on hear blade 30, as shown by arrow A moves the distal end of heart blade 30 downward, as shown by arrow B.

Figure 7:
FIG. 7 depicts a partially cutaway, perspective view of the patient's chest cavity

In FIG. 7, a partially cutaway, perspective view of the patient's chest cavity is depicted. In this view, heart blade 30 is shown pushing downward on the patient's heart 1030 in accordance with the depiction in FIG. 6.

Endoscope Holder

Figure 8:
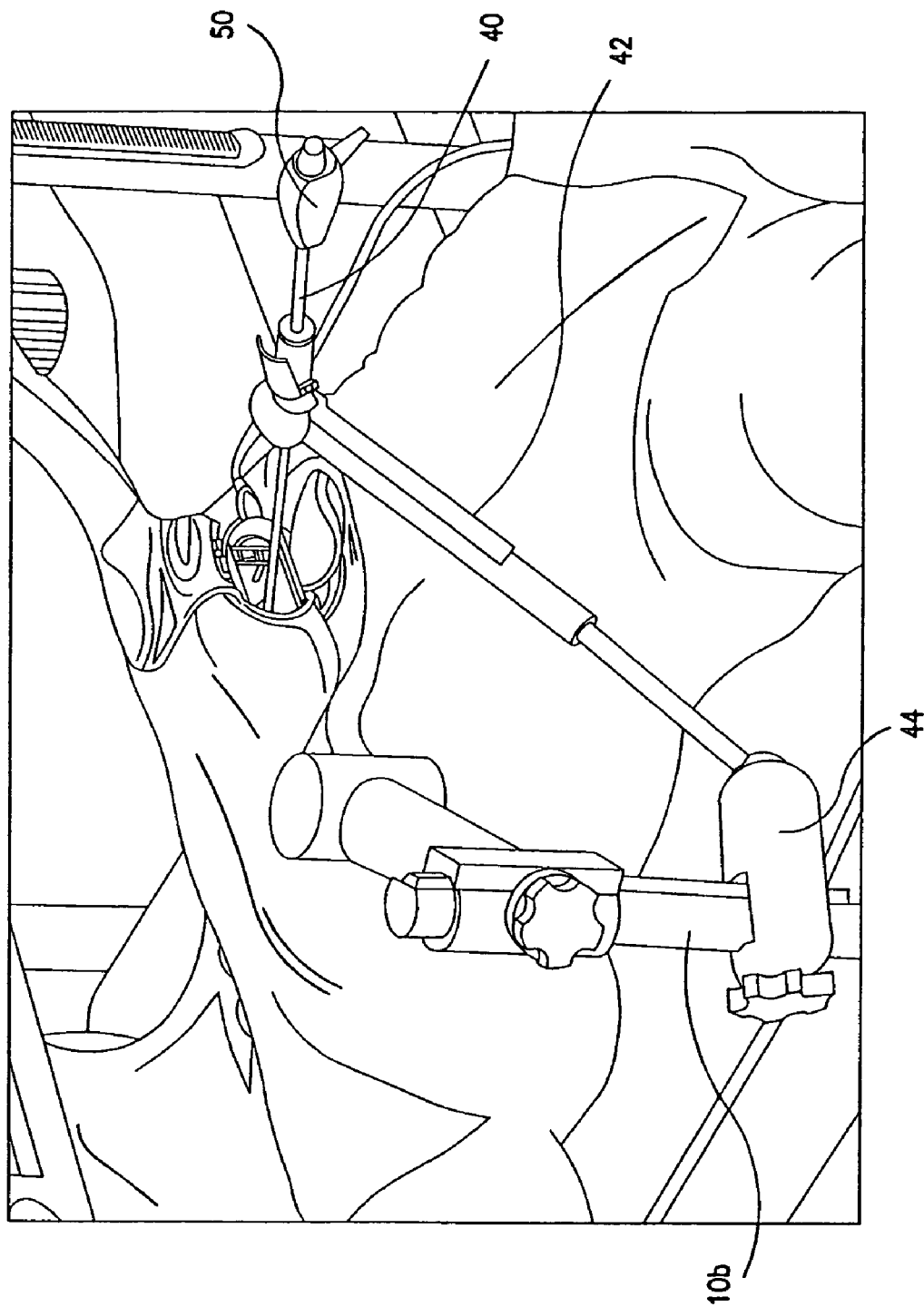
FIG. 8 depicts an endoscope holding device with the endoscope in place.

As shown in FIG. 8, an endoscope 40 equipped with a camera 50 may be used to visualize the inside of the patient's chest cavity. Images captured by camera 50 may be displayed on monitor 220. Endoscope 40 may be inserted into the patient's chest cavity through window-like opening 15 in fulcrum device 14. An endoscope holding device 42 may be used by the surgeon to manipulate endoscope 40 in a desired position. An endoscope stabilizing device 44, which may be used to stabilize endoscope 40 within the patient's body during surgery, may be attached to one of the vertical bars, such as second vertical bar 10*b*, of surgical table 200.

Figure 9:
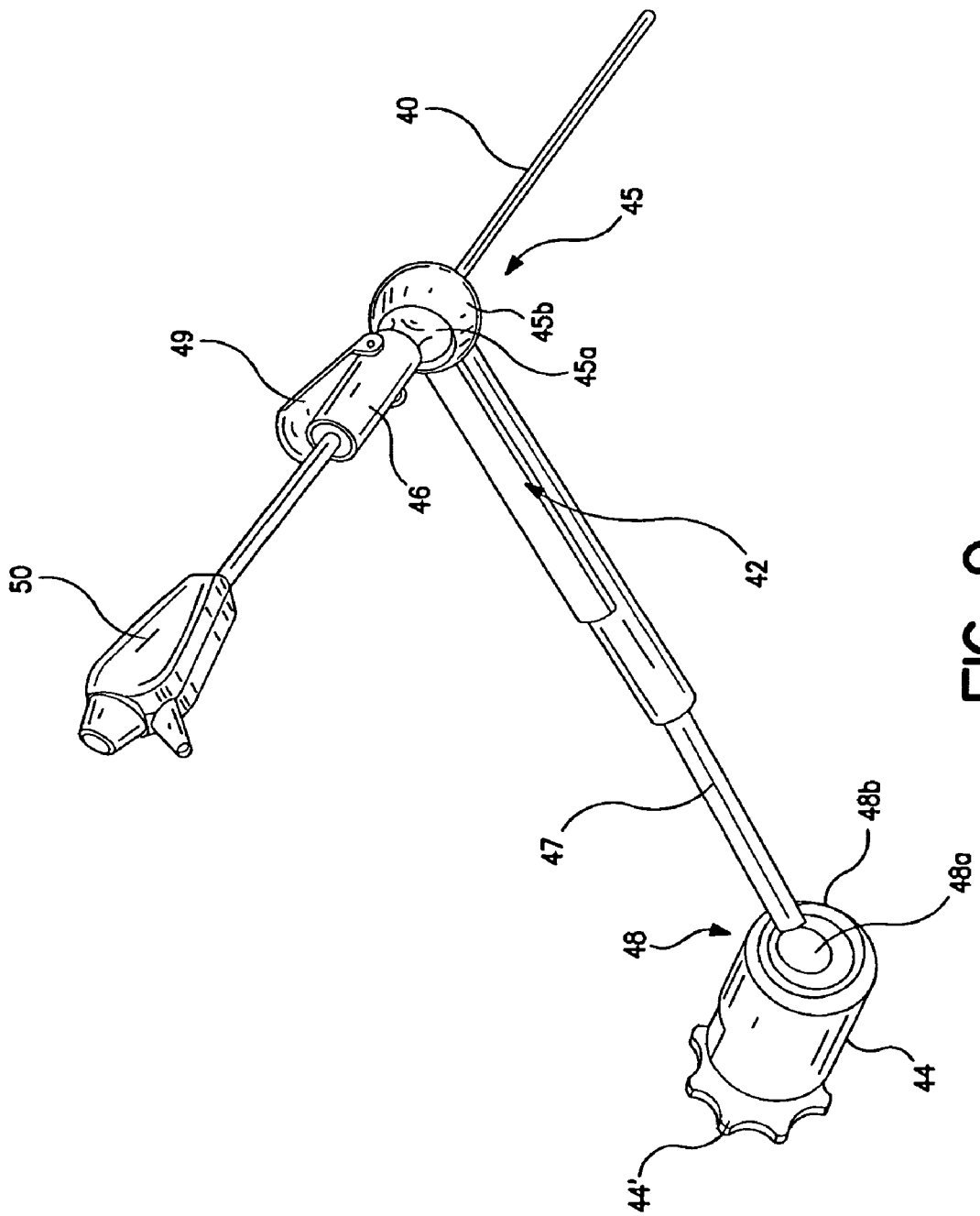
FIG. 9 depicts the endoscope and the endoscope holding device.

An embodiment of endoscope 40 including camera 50 is depicted in FIG. 9. Endoscope stabilizing device 44 secures the shaft of endoscope 40 to second vertical bar 10*b*. A knob screw 44' helps secure endoscope stabilizing device 44 to second vertical bar 10*b*.

The shaft of endoscope 40 passes through a first ball joint 45 and a handle 46. Handle 46 is equipped with a mechanism for applying friction to the shaft of endoscope 40 to prevent the shaft of endoscope 40 from moving in and out. First ball joint 45 comprises a first ball 45*a* and a first socket 45*b*, which is engaged first ball 45*a*. A manipulating shaft 47 rides in and out of endoscope holding device 42, and a second ball joint 48 supports manipulating shaft 47 and rides inside second socket 47*b*. Second ball joint 48 comprises second ball 48*a* and second socket 48*b*. Generally, first ball joint 45 and second ball joint 48 are fixed in position by the surgeon, whereby first ball 45*a* and second ball 48*a* engage or are engaged by first socket 45*b* and second socket 48*b*, respectively, to hold endoscope 40 in a desired position.

In a preferred embodiment, when an activating lever 49 is depressed, each of ball joints 45 and 48 are unencumbered, such that first ball 45*a* and second ball 48*a* may move freely within first socket 45*b* and second socket 48*b*, respectively. For example, when activating lever 49 is depressed; mechanical, electrical, or electromagnetic signals, or the like, may be transmitted via handle 46 and manipulating shaft 47 to actuate one, either, or both of ball joints 45 and 48. Consequently, the surgeon may manipulate endoscope 40 freely with respect to manipulating shaft 47, and endoscope 40 may be moved to any position in space. When the lever 45 is released, each of the ball joints locks into position and holds endoscope 40 in the desired position.

Dissecting Instrument

Figure 10:
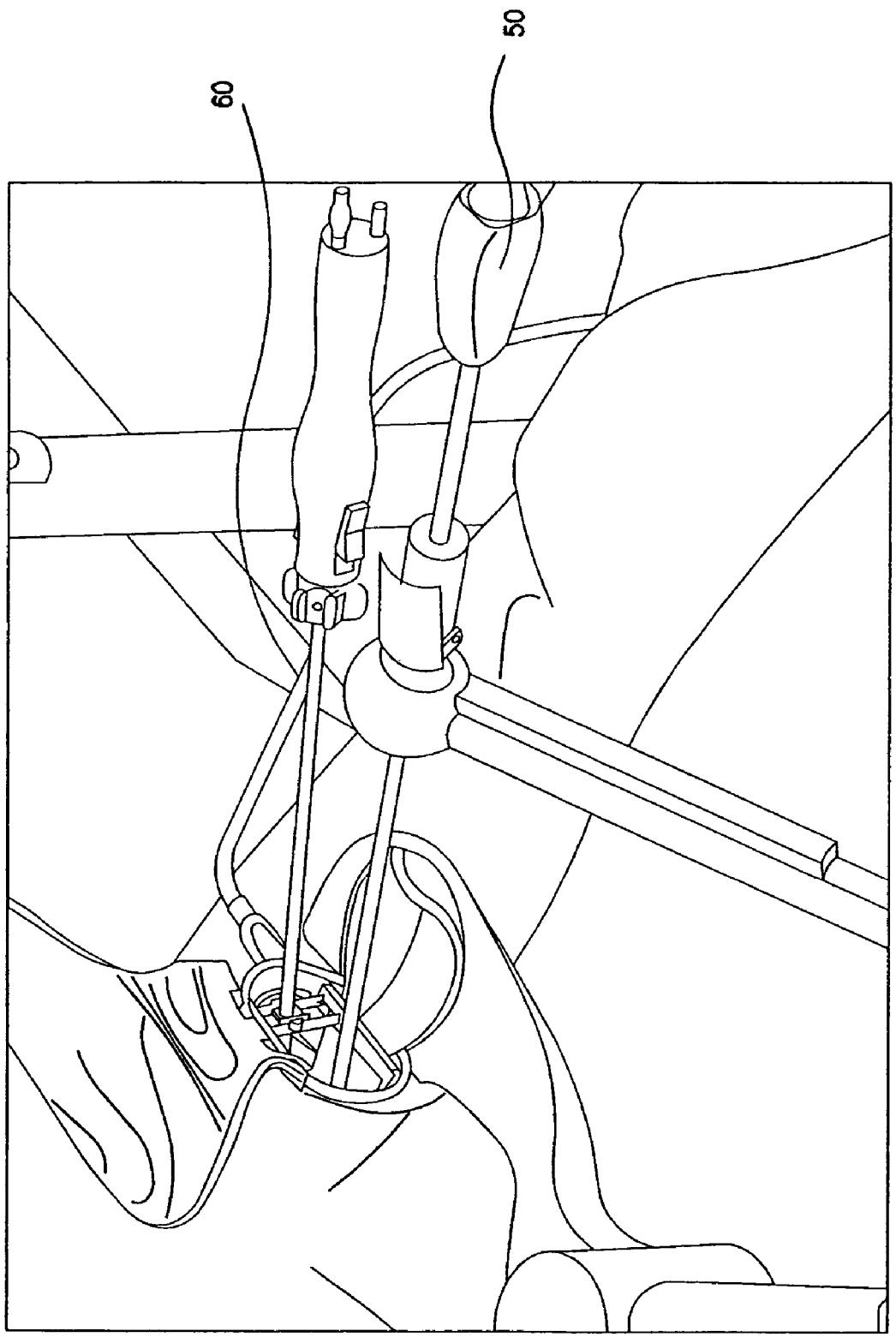
FIG. 10 depicts the endoscope and a dissecting instrument positioned through the fulcrum device into the chest cavity.

A dissecting instrument 60 of FIG. 10 may be used together with endoscope 40 in surgical procedures on patient 1000. As shown in FIG. 10, both the dissecting instrument 60 and endoscope 40 may enter the patients chest cavity through window-like opening 15 of fulcrum device 14. In particular, however, dissecting instrument 60 may be inserted into the patient's chest cavity through the instrument access orifice of instrument port 21.

Figure 11:
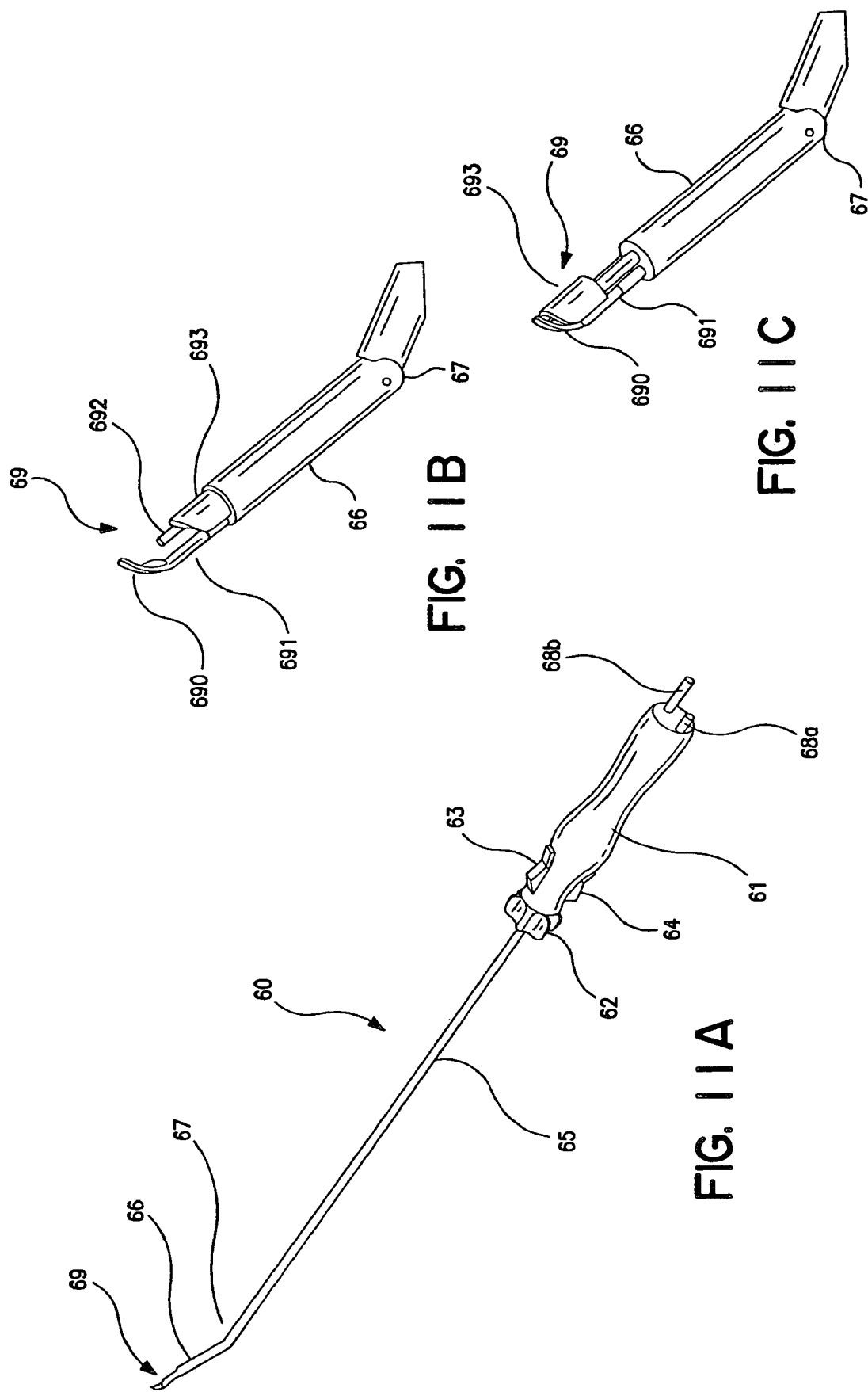
FIG. 11A depicts a dissecting instrument.
FIGS. 11B and 11C depict enlarged views of the tip of the dissecting instrument of FIG. 11A and illustrate the multiple functions of an embodiment of the dissecting instrument.

Referring to FIG. 11A, dissecting instrument 60 comprises a handle 61, shaft 65, and tip 69. Tip 69 comprises dissecting means. Dissecting instrument 60 may perform at least three separate functions: first, blunt dissection with spatula-shaped tip 69; second, injection of $CO_2$ at the distal end to separate tissue planes; and third, coagulation and cutting by RF energy. Shaft 65 and tip 69 are rotatable by means of rotation control knob 62. Moreover, a distal end 66 of shaft 65 may be pivotable at a shaft joint 67. A first slidable button 63 may be provided on handle 61 to articulate distal end 66 about shaft joint 67.

As noted above, dissecting instrument 60 may be used to perform multiple functions. Referring to FIGS. 11B and 11C, enlarged views of tip 69 are depicted. A spatula end 690 affixed to spatula end shaft 691 may be used as a blunt dissector. A second slidable button 64 on handle 61 may be actuated to move a grasper jaw 693 into and out of contact with spatula end 690. For example, when second slidable button 64 on handle 61 is actuated; mechanical, electrical, or electromagnetic signals, or the like, may be transmitted via shaft 65 to move a grasper jaw 693 into and out of contact with spatula end 690. Handle 61 also may be equipped with means for conveying $CO_2$ and RF energy to tip 69. For example, a $CO_2$ connection 68*a* in handle 61 may be connected to a supply source for $CO_2$. $CO_2$ may be passed from the $CO_2$ connection 68*a* through dissecting instrument 60 to a $CO_2$ outlet tube 692 located in tip 69. When tip 69 is properly positioned and the flow of $CO_2$ is activated, $CO_2$ is injected into the patient's tissue, which is engaged at the distal end of tip 69 of dissecting instrument 60. The flow of $CO_2$ enables the surgeon to separate tissue into natural tissue planes. In this way, the vessel being dissected is more easily identified and dissected out of the tissue.

As noted above, dissecting instrument 60 also may utilize RF energy in the removal of a vessel. For example, an RF connection 68b in handle 61 may connect dissecting instrument 60 to a known RF energy console. If a blood vessel is encountered requiring coagulation, e.g., cauterization, the surgeon may manipulate second slidable button 64 on handle 61 to grasp the vessel between spatula end 690 and grasper jaw 693. The surgeon then may apply RF energy to the vessel in order to seal the vessel. Once the vessel has been sealed, the surgeon again may manipulate second button 64 to move grasper jaw 693 away from spatula end 690 and placing the sealed vessel in direct contact with the edge of spatula end shaft 691. With the exception of a narrow strip along its innermost surface, the contacting edge of spatula end shaft 691 is electrically insulated along its length. When the RF energy is applied to this spatula end shaft 691, the RF energy is focused onto the vessel's tissue along this narrow, uninsulated strip and the tissue is cut by the RF energy, thereby severing the sealed vessel into two portions.

Figure 12:
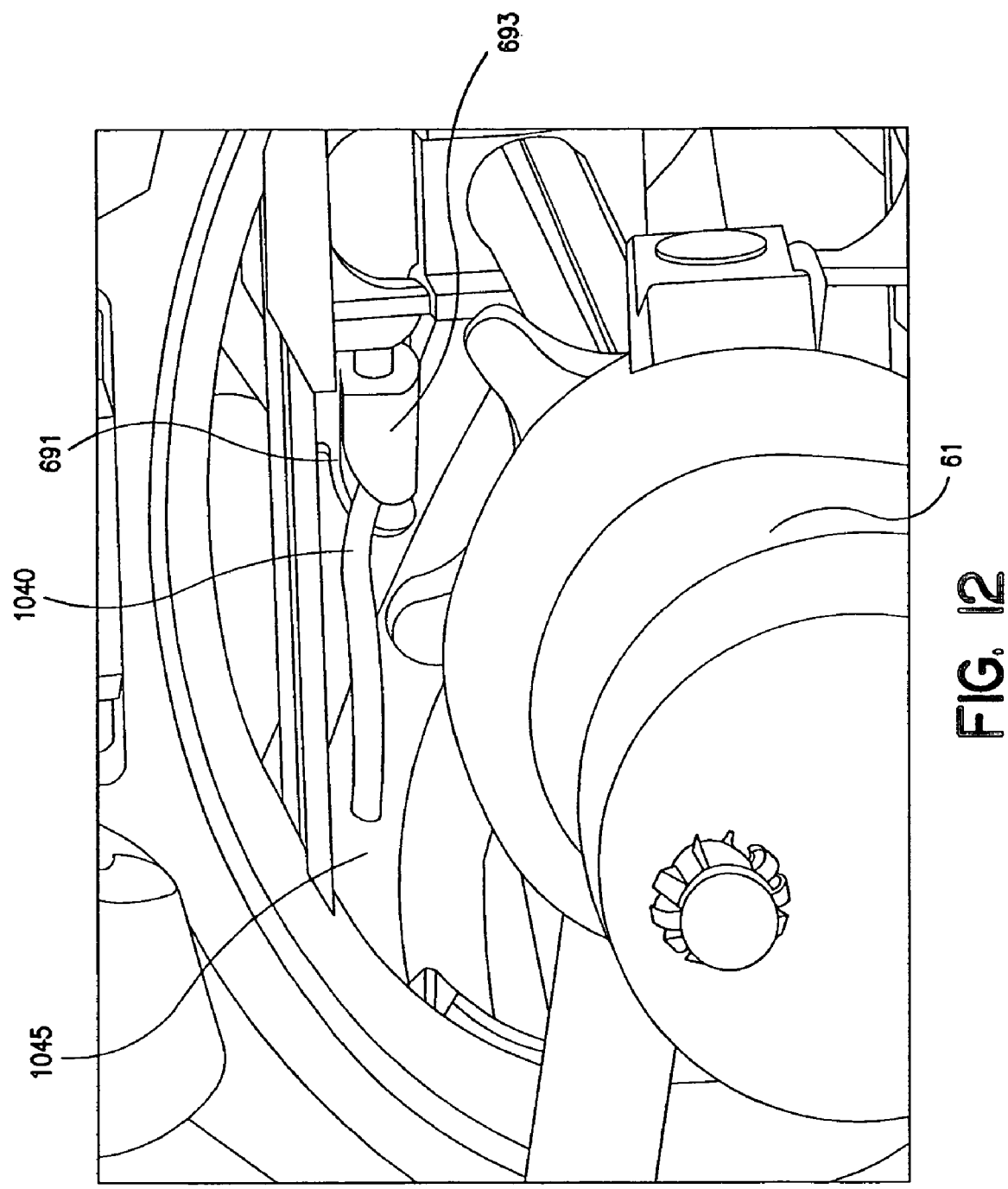
FIG. 12 depicts the dissecting instrument grasping a branch of the Internal Mammary Artery

Use of dissecting instrument 60 is shown in FIG. 12. Dissecting instrument 60 is shown grasping a blood vessel 1040 which is a branch of the Internal Mammary Artery (IMA) 1045. The vessel 1040 is grasped between spatula end 690 and grasper jaw 693, and RF energy then may be applied to coagulate blood within the vessel.

Left Ventricular Cannula

Figure 13:
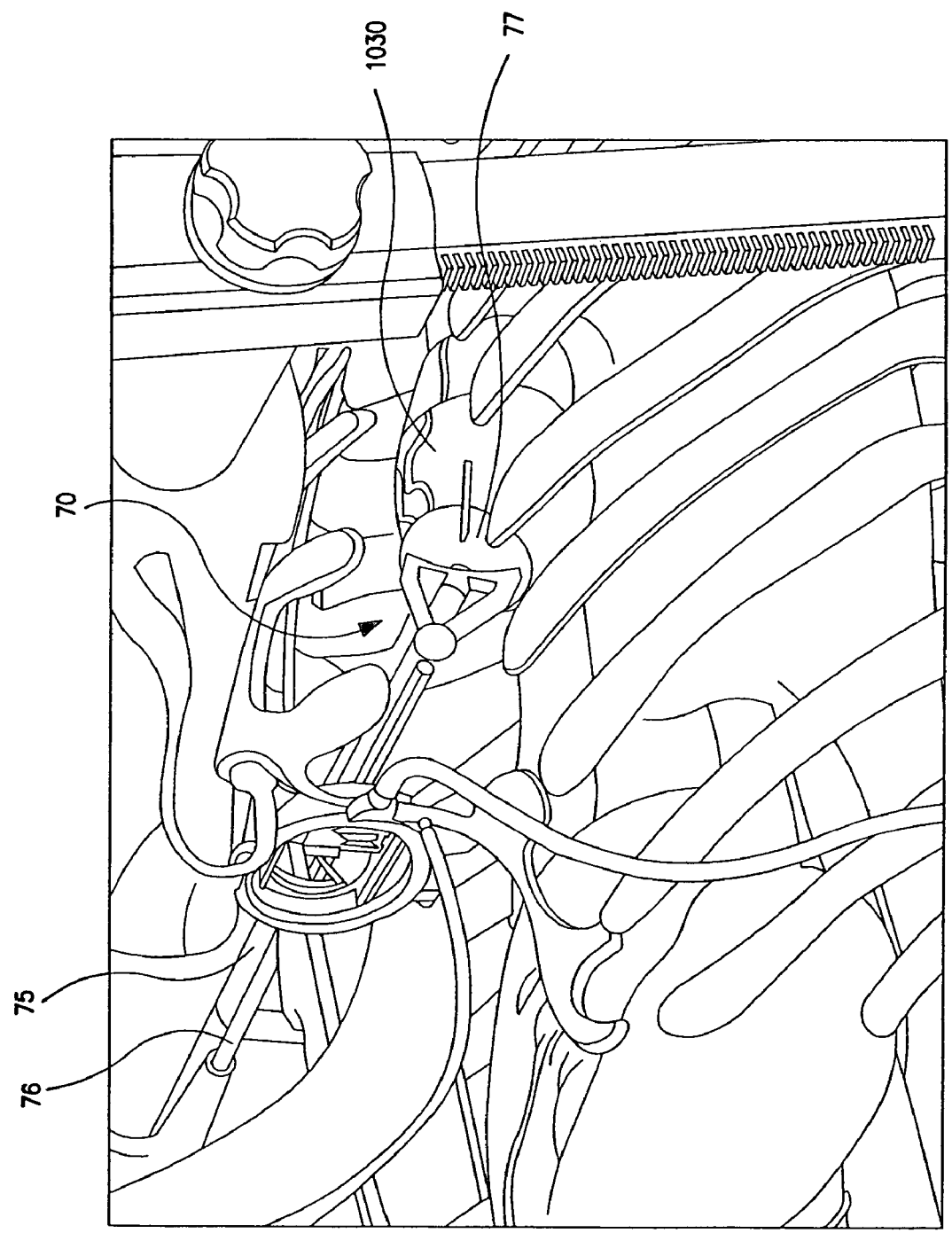
FIG. 13 depicts a partially cutaway, side perspective view of the patient's chest with the cannula in place.

A partially cutaway, side perspective view of the chest is shown in FIG. 13. An Left Ventricular (LV) cannula 70 is a catheter and heart manipulation device. Cannula 70 may be used to deliver blood to the aorta or cardioplegia solution to the coronary arteries, or both, during CPB.

Referring to FIG. 14, a cross-section of heart 1030 is shown with LV cannula 70 in place. LV cannula 70 is positioned with a cannula tip 71 in the ascending aorta 1033. A distal balloon 72 is inflated in the aorta 1033 to seal the aorta 1033 and stabilize cannula tip 71. A second balloon 73 is positioned inside the left ventricle 1034 and serves to center cannula 70 within the left ventricle 1034. LV cannula 70 is attached to the heart 1030 via a suction cup 77 affixed on the left ventricular apex 1035. The surgeon may employ a manipulator arm 76 attached to suction cup assembly 77 to manipulate the heart 1030 during surgery, in particular, to gain access behind the heart 1030. Catheter tubing 75 exits the heart 1030 through suction cup assembly 77. Catheter tubing 75 may be attached to CPB machinery or other known cardiopulmonary support systems. Oxygenated blood may be pumped from CPB machinery, through catheter tubing 75 and out the cannula tip 71, as such blood is delivered to patient 1000. In addition, cardioplegia solution which is used to stop the heart from beating may be pumped from outside patient 1000, through one of catheter tubes 75. Such cardioplegia solution exits the cannula from holes 78 located distal to the aortic valve, but proximal to distal balloon 72 to enter the coronary arteries in the coronary sinus.

Figure 15B:
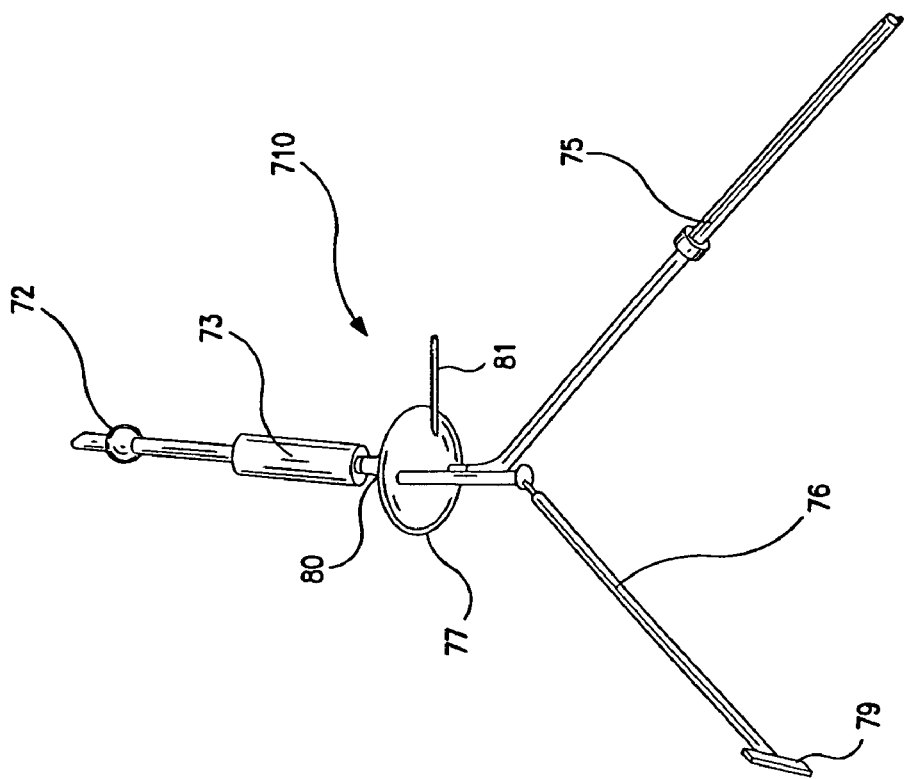
FIG. 15B depicts the entire cannula outside of the patient's heart.
Figure 15A:
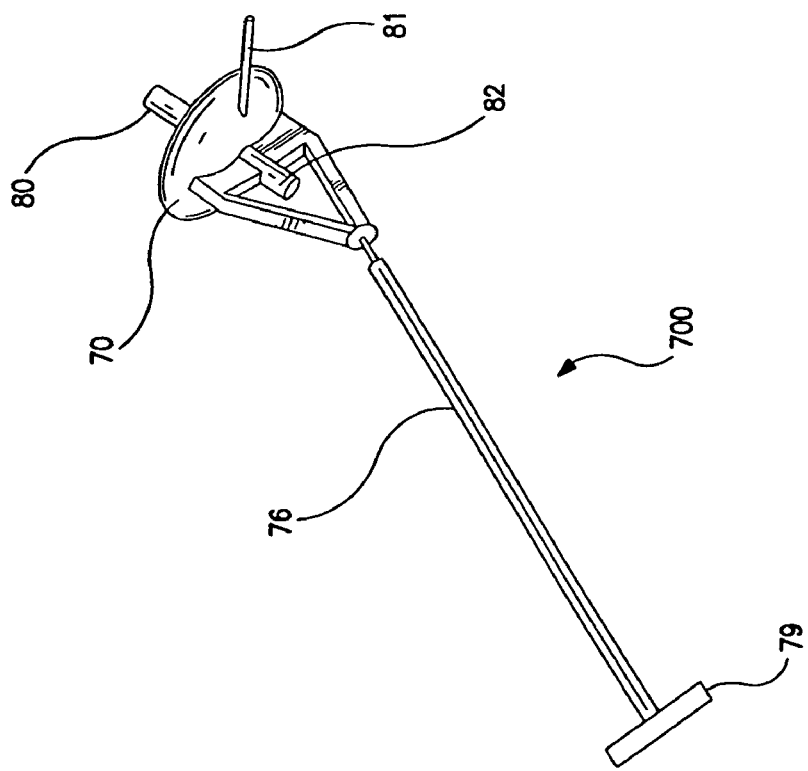
FIG. 15A depicts the manipulation and attachment features of the cannula.

LV cannula 70 comprises two components: a stabilizer and manipulation component 700 depicted in FIG. 15a and a catheter component 710 added in the depiction of FIG. 15b. Stabilizer and manipulation component 700 is introduced through an incision made in the apex 1035 of the heart 1030, for example, using either a scalpel or a trocar. Stabilizer and manipulation component 700 comprises a stabilizer shaft 80, which penetrates through the wall of the apex 1035 of the left ventricle 1034 and into the left ventricle 1034. The surgeon may apply suction to suction cup 77 through a suction tube 81. The suction is transferred through holes on the inside of suction cup 77 and draws suction cup 77 onto the muscle tissue of the left ventricle 1034. A handle 79 is pivotally mounted to stabilizer and manipulation component 700, and the surgeon may employ handle 79 to manipulate cannula 70 and, therefore, the heart 1030. Stabilizer and manipulation component 700 further may comprise a hemostatic valve 82 which permits passage of a device through suction cup 77 of cannula 70, but limits blood flow back through valve 82.

Once stabilizer and manipulation component 700 has been applied, the surgeon may pass catheter component 710, as shown in FIG. 15B, through stabilizer and manipulation component 700 and through the left ventricle 1034 until cannula tip 71 rests in the ascending aorta 1033. The surgeon may pass catheter component 710 through hemostatic valve 82 which seals around catheter component 710 and prevents leakage of blood.

Proximal balloon 73 serves to center catheter component 710 in the left ventricle 1034 and also to limit any movement of catheter component 710 linearly. A cross-sectional view of proximal balloon 73 is depicted in FIG. 15D. The shaft of catheter component 710 passes through a lumen 730 formed within proximal balloon 73. Proximal balloon 73 may be bonded to the shaft along the center of lumen 730 of proximal balloon 73 at an interior surface 731. Thus, proximal balloon 73 is free to move at its ends 732. This design permits the shaft limited axial movement, as shown by double-headed arrow C of FIG. 15C. Such axial movement is necessary because, as oxygenated blood is injected through catheter component 710 into the aorta 1033, a hydraulic force is created pushing catheter component 710 towards the heart 1030.

Such oxygenated blood exits catheter component 710 at a distal discharge opening 83 in FIG. 15E. Distal discharge opening 83 is angled to deflect the blood away from the aorta 1033 and, thereby, to avoid direct jetting of blood against the aorta walls. Unlike oxygenated blood, cardioplegia solution exits catheter component 710 from radial discharge openings 78 adjacent to proximal balloon 72.

Tissue Scissors

Figures 16A, 16B:
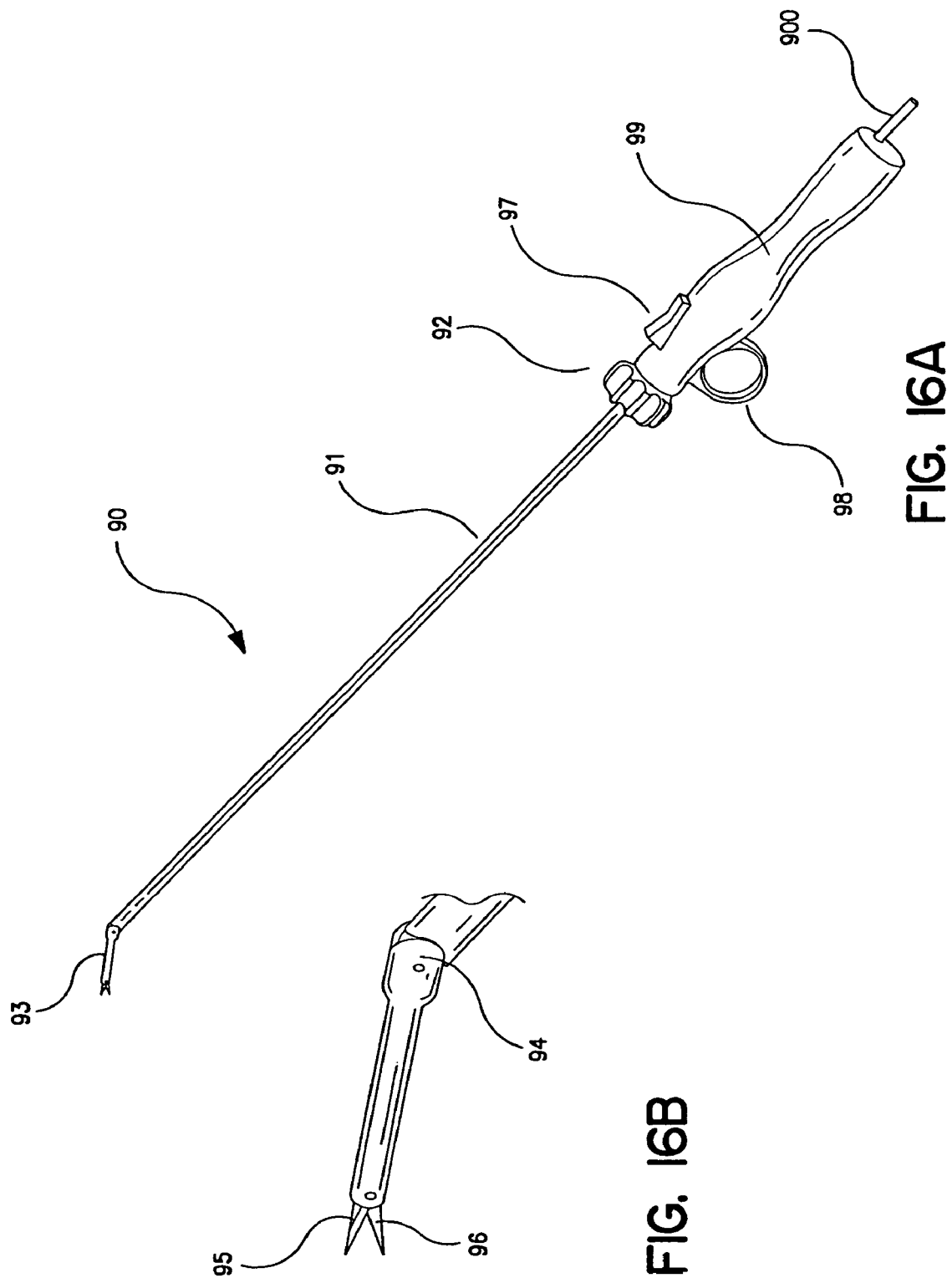
FIG. 16A depicts a pair of cardiac scissors.
FIG. 16B depicts and enlarged view of the tip of the cardiac scissors of FIG. 16A.

Referring to FIGS. 16A and 16B, a scissors 90 may be used by the surgeon to dissect tissue or to cut an incision into a vessel to allow placement of a coupler. Scissors 90 also may be used as an alternative to dissecting instrument 60 of FIGS. 11A-11C. A scissors handle 99 is attached to a scissors shaft 291. A distal end 93 of scissors 90 is adapted to pivot about a distal end joint 94 by manipulating a slidable button 97. Scissors 90 may be equipped with two counter acting scissor blades 95 and 96 at its distal end. An inner shaft (not shown) may be translated by manipulation of a handle ring 98. The manipulation of ring 98 further manipulates either or both of scissor blades 95 or 96. For example, when ring 98 is manipulated; mechanical, electrical, or electromagnetic signals, or the like, may be transmitted via scissors shaft 291 to move either or both of scissor blades 95 or 96 into contact with each other. In still another embodiment of such scissors, scissors 90 may be adapted to employ RF energy if a blood vessel is encountered requiring coagulation, e.g., cauterization. Similar to the forgoing description of dissecting instrument 60 of FIG. 11A, an RF connection 900 in handle 99 may connect at least one of scissor blades 95 and 96 of scissors 90 to a known RF energy console.

Vascular Connections

As shown in FIGS. 17-20, a coupler 100 according to an embodiment of the present invention comprises a saddle 101 for positioning within a conduit and a channel 102 for directing fluid from the conduit through coupler 100. Coupler 100 further comprises a tissue clamp 103 for securing the conduit to saddle 101, a flange 106 for positioning in alignment with a flange 106 of another coupler 100, and a mating surface 107, 107' for attachment to a mating surface 107, 107' of another coupler 100.

Figure 29:
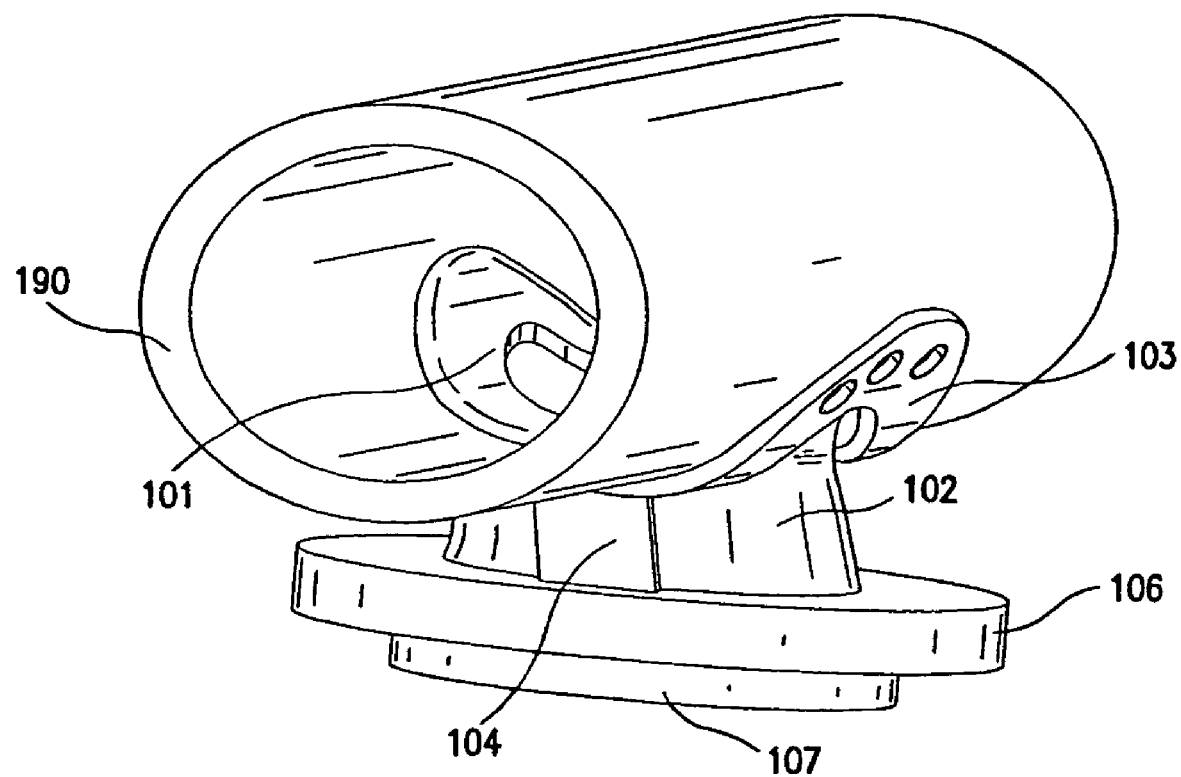
FIG. 29 depicts a view of coupler positioned in and secured to a conduit.

Saddle 101 has a substantially elliptical cross-section and may be positioned within a conduit. As shown in FIG. 29, saddle 101 may be configured with a curvature that is the same as, or substantially similar to, a curvature of the inner and outer surfaces of conduit 190 in which saddle 101 may be positioned. The curvature of saddle 101 may be varied depending upon the curvature of conduit 190, so that an area of contact between saddle 101 and conduit 190 may be increased or so that conduit 190 may not be distorted by placement of saddle 101 within conduit 190, or both.

Saddle 101 may be positioned within a conduit by making an incision at a desired location along conduit 190. The length of the incision may be less than a length of the longest axial dimension of saddle 101. Saddle 101 then may be inserted through the incision into conduit 190. Conduit 190 may stretch slightly to fit over the edges of saddle 101 as saddle 101 is positioned within conduit 190.

Figure 17:
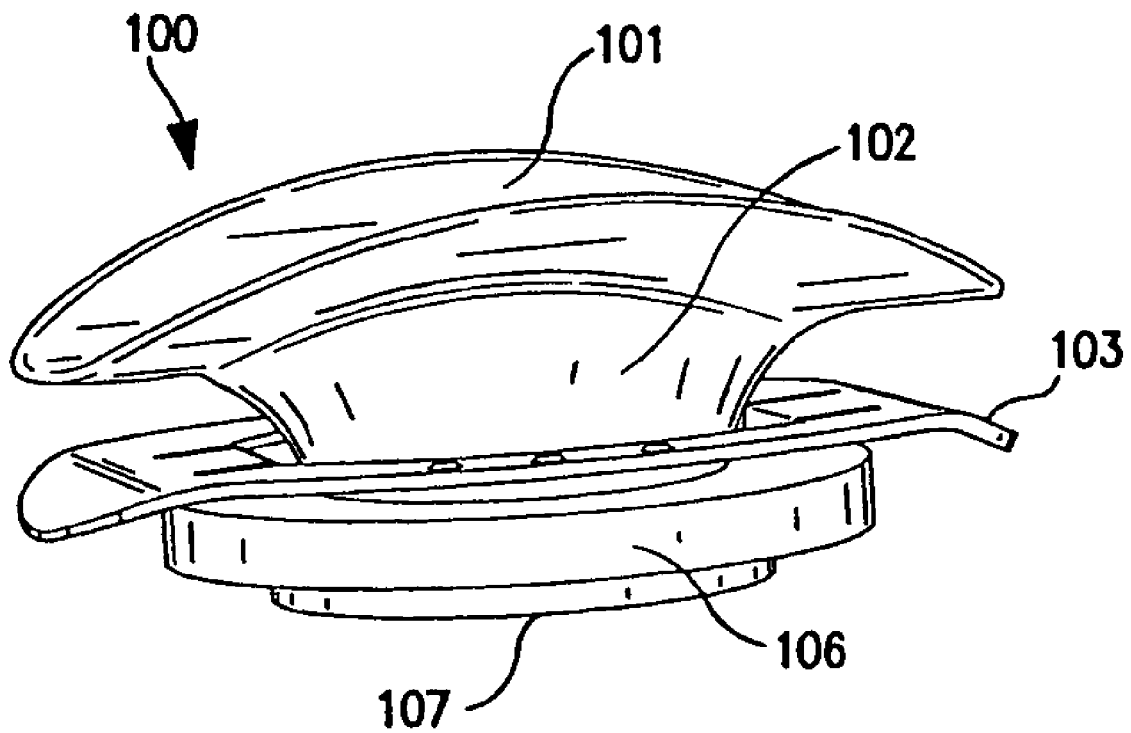
FIG. 17 depicts a coupler with the tissue clamp in a relaxed state.
Figure 28:
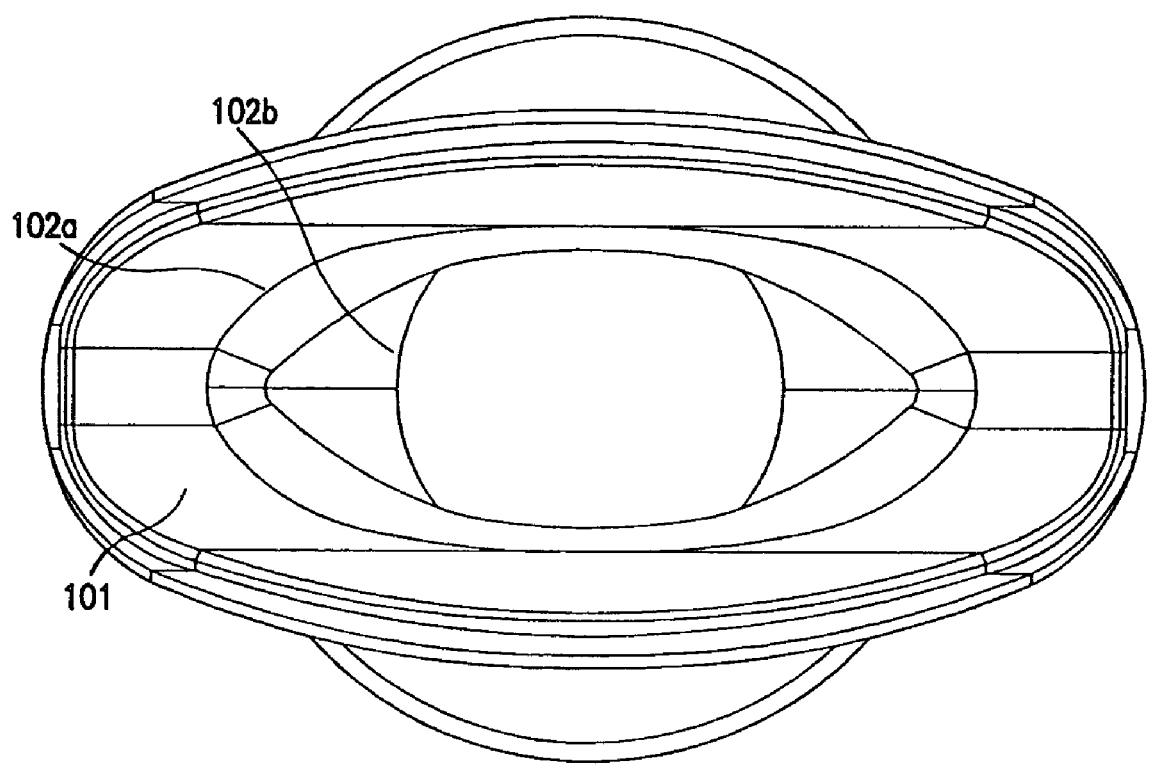
FIG. 28 depicts a top view of a coupler according to an embodiment of the present invention.

Saddle 101 transitions to a channel 102, which may be formed integrally with saddle 101, as shown in FIG. 17. When saddle 101 is positioned within conduit 190, channel 102 remains entirely or substantially outside of conduit 190, as shown in FIG. 29. Channel 102 forms a flow path for fluid in conduit 190 to flow through coupler 100. As shown in FIG. 28, an inner surface of channel 102 transitions from a substantially elliptical cross-sectional area 102*a* to a substantially circular cross-sectional area 102*b*.

In one embodiment of the invention, the cross-sectional area of channel 102 remains substantially constant as the inner surface of channel 102 transitions from an area of substantially elliptical cross-section 102*a* to an area of substantially circular cross -section 102*b*. This configuration improves the ability of channel 102 to direct fluid through coupler 100 at a substantially constant velocity or rate, or both, with a minimum of disturbances in the fluid flow. In addition, the cross-sectional area of each channel 102 may correspond to the cross-sectional area of a conduit in which coupler 100 may be positioned, so that the velocity or rate, or both, of fluid flowing from conduit 190 through coupler 100 may remain substantially constant. In another embodiment of the invention, the cross-sectional area of channel 102 may increase or decrease as channel 102 transitions from an area of substantially elliptical cross-section 102*a* to an area of substantially circular cross-section 102*b*, so that coupler 100 may be used to connect conduits 190 of different cross-sectional areas.

Figure 19:
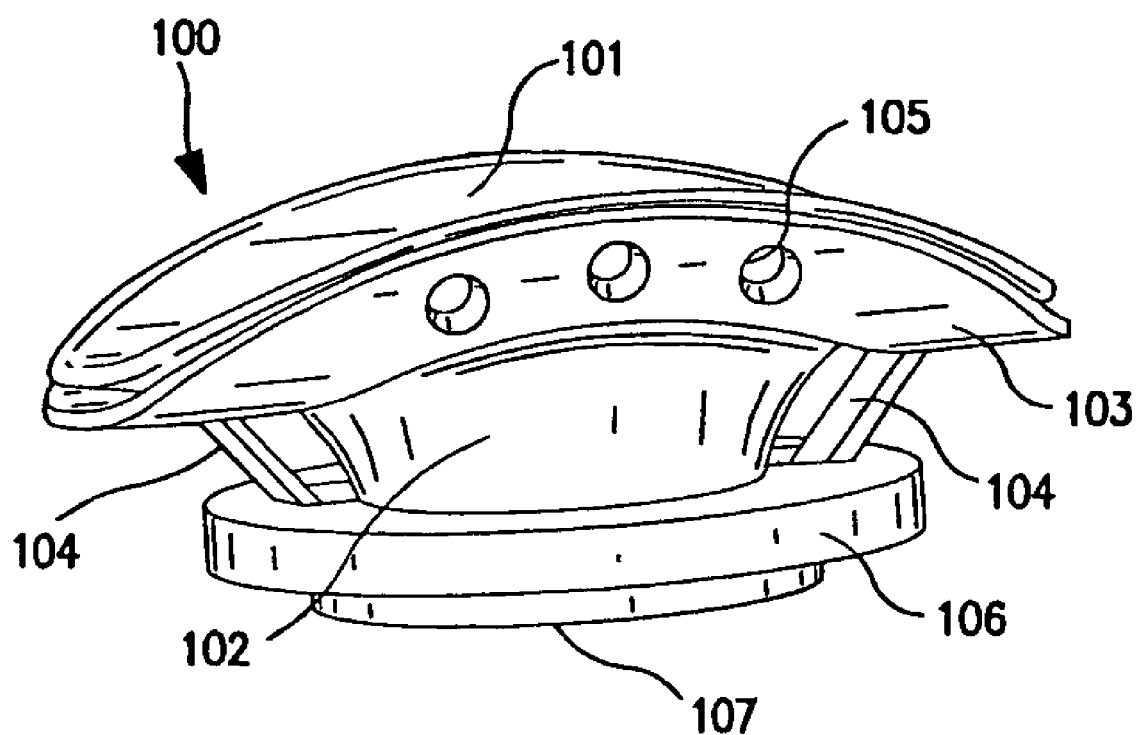
FIG. 19 depicts a coupler after a tissue clamp is heated to its transition temperature.
Figure 20:
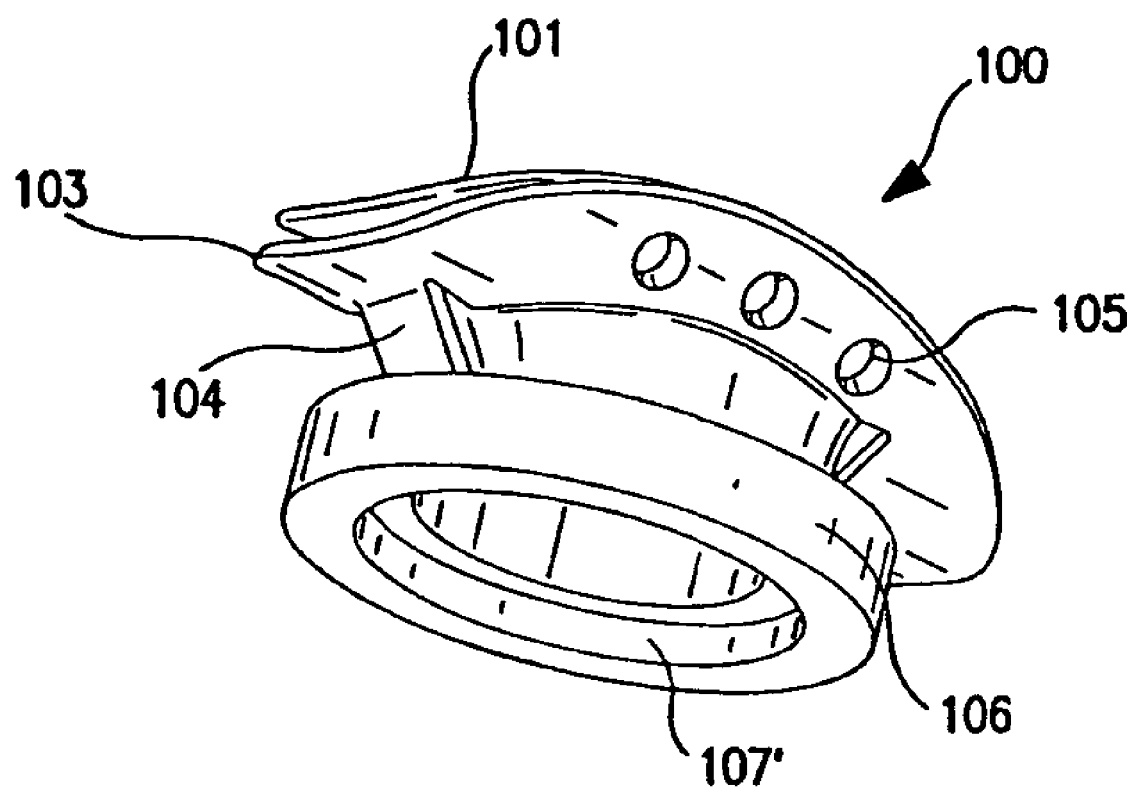
FIG. 20 depicts a coupler with complementary mating surface.
Figure 21:
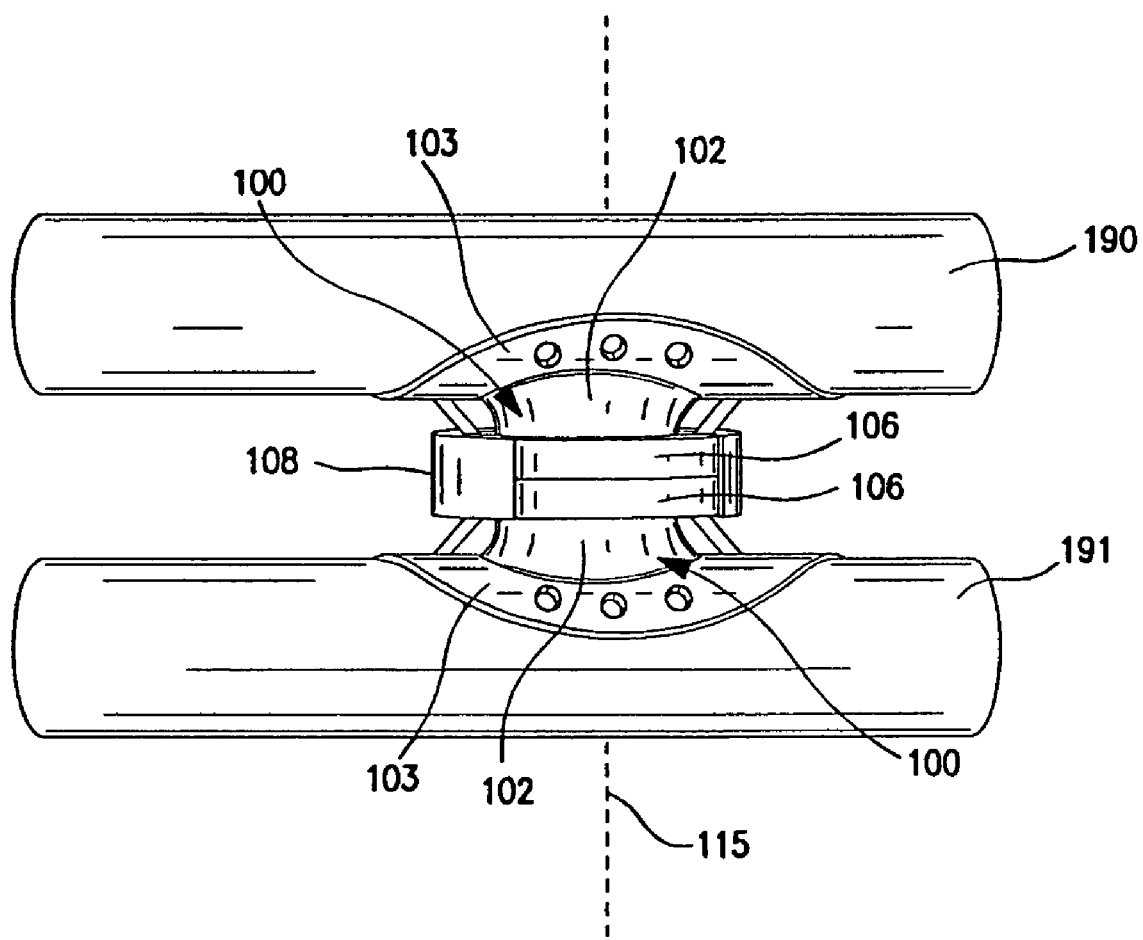
FIG. 21 depicts a conduit coupling device connecting two conduits.

A flange 106 and a mating surface 107, 107' may be formed at an end of channel 102. For example, flange 106 may be formed along an outer surface of channel 102, adjacent to a portion of channel 102 having a substantially circular cross-section, as shown in FIGS. 17-20. Flange 106 and mating surface 107, 107' enable a pair of couplers 100 to be secured together to form a conduit coupling device according to the present invention for connecting two conduits. By positioning flange 106 and mating surface 107, 107' of one coupler 100 in alignment with flange 6 and complementary mating surface 107, 107' of another coupler, as shown in FIG. 21, two conduits may be placed in fluid communication. In one embodiment of the invention, mating surfaces 107, 107' may comprise complementary indented and protruding stepped portions that may be formed on respective flanges 106 of a pair of couplers 100.

Figure 18A:
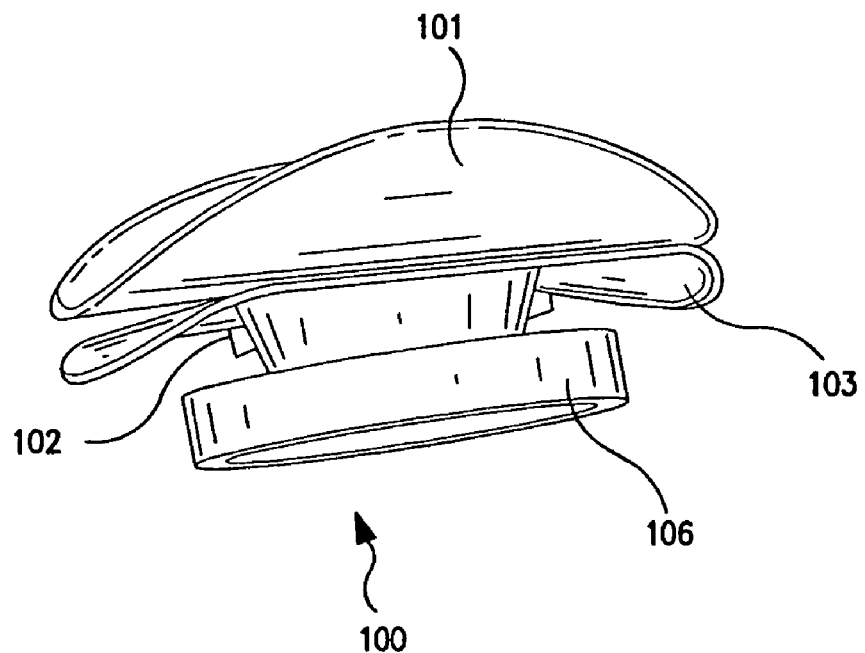
FIGS. 18A and 18B depicts the vessel connection devices as the tissue clamp deploys.
Figure 18B:
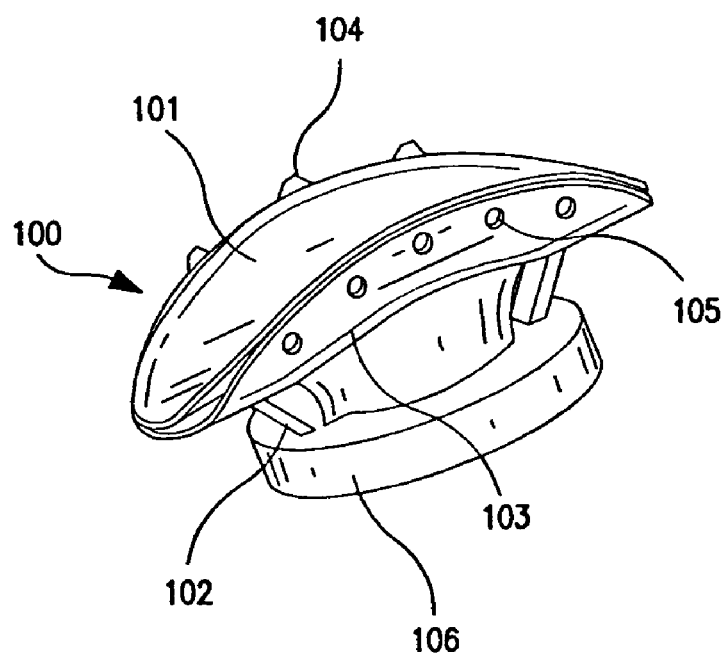

The connector is shown in more detail in FIGS. 18A and 18B. Each connector comprises saddle 101, tissue clamp 103, and flange 106. Tissue clamp 103 maybe made from a superelastic material, such as nitinol. Tissue clamp 103 may be held by the delivery device, such that tissue clamp 103 is pulled back from saddle 101 to permit saddle 101 to be introduced into the vessel. Once saddle 101 is introduced into the vessel, tissue clamp 103 is released and springs into the position shown in FIG. 18B.

Figure 24:
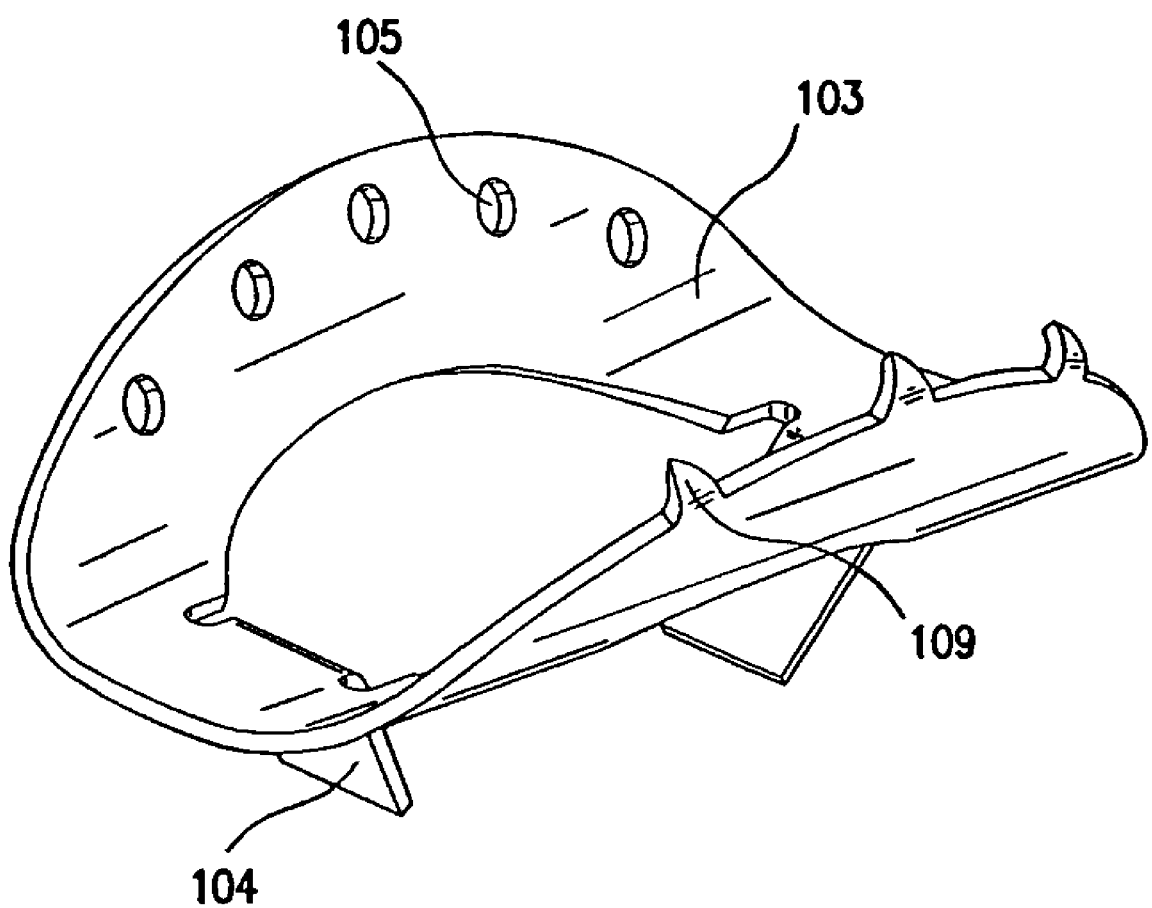
FIG. 24 depicts a clamping ring with teeth and holes.

Tissue clamp 103 may be positioned around channel 102. Tissue clamp 103 remains outside of conduit 190. Tissue clamp 103 may comprise legs 104 and a plurality of holes 105. Holes 105 may be formed through tissue clamp 103. Holes 105 improve the connection between tissue clamp 103 and tissue of conduit 190, thereby securing conduit between tissue clamp 103 and saddle 101. Holes 105 may be dimpled, as shown in FIGS. 19 and 20, so that holes 105 protrude toward and into tissue of conduit 190 to improve further the connection between tissue clamp 103 and conduit 190. In addition, tissue may grow through holes 105, further securing tissue clamp 103 and coupler 100 to conduit 190. In another embodiment of the invention, a plurality of teeth 109 may be positioned along a periphery of tissue clamp 103 to engage tissue of conduit 190, thereby securing conduit 190 between tissue clamp 103 and saddle 101. In a further embodiment of the invention, tissue clamp 103 may include a plurality of holes 105 and teeth 109, as shown in FIG. 24.

Figure 22:
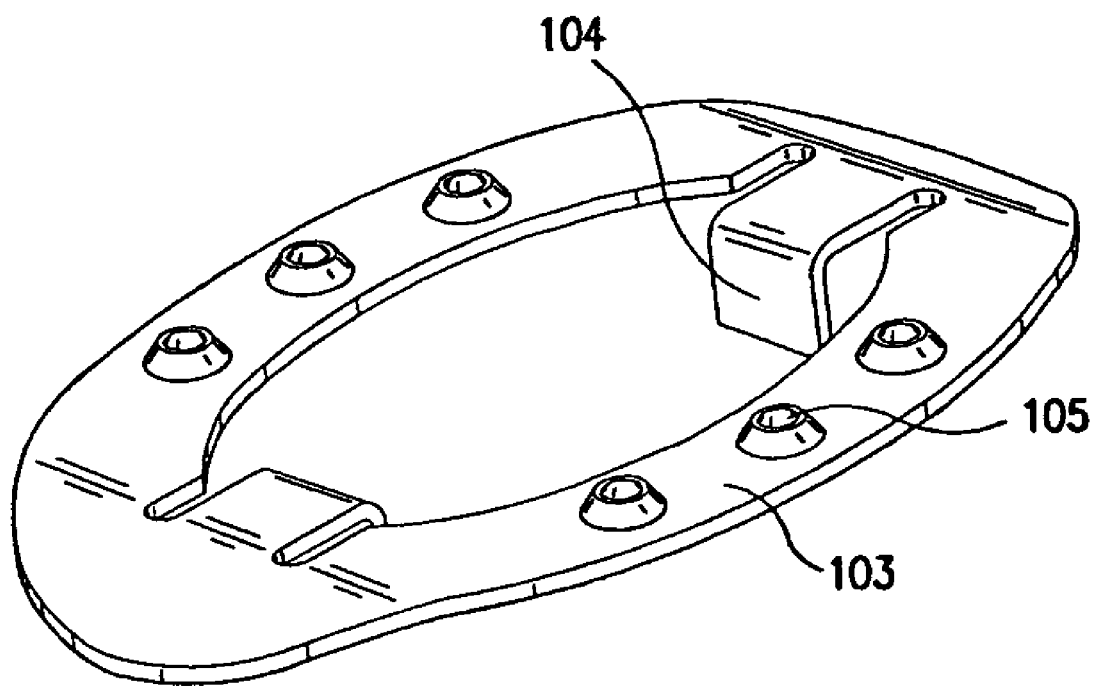
FIG. 22 depicts a clamping ring in a martensitic state.

Tissue clamp 103 may be formed of a shape-memory alloy, such as a nickel titanium alloy or the like. The transition temperature of the shape-memory alloy may be selected to be a temperature that is at or slightly above body temperature, such as 38° C. for humans. Therefore, tissue clamp 103 may be ductile and easily shaped at room temperature in its martensitic state. In one embodiment of the invention, tissue clamp 103 may be shaped into a substantially flat form in its martensitic state, as shown in FIGS. 17 and 22, and tissue clamp 103 may be positioned adjacent to flange 106 of coupler 100. This configuration enables saddle 101 of coupler 100 to be positioned within a conduit without tissue clamp 103 interfering with the positioning of saddle 101.

Figure 23:
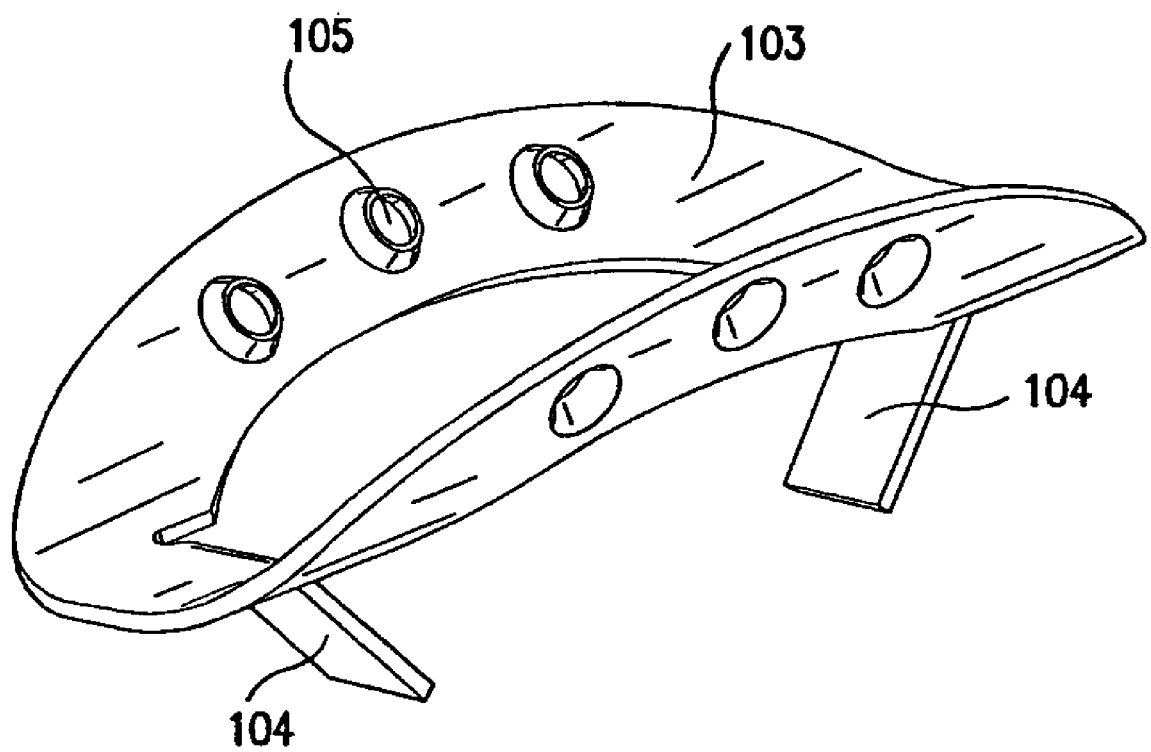
FIG. 23 depicts a clamping ring that is heated to its transition temperature.

Tissue clamp 103 maintains its martensitic state shape until tissue clamp 103 is heated to its transition temperature, which in one embodiment of the invention may be selected to be a temperature that is at or above human body temperature. Once tissue clamp 103 is heated to its transition temperature, tissue clamp 103 transforms, i.e., returns to a predetermined shape, which may be a shape shown in FIGS. 19, 20, and 23, in which tissue clamp 103 secures a conduit between tissue clamp 103 and saddle 101. Tissue clamp 103 may have a predetermined shape in which legs 104 of tissue clamp 103 extend and sides of tissue clamp 103 curve upward and assume a substantially elliptical curved shape to secure conduit 100 between tissue clamp 103 and saddle 101, as shown, for example, in FIG. 29. Each leg 104 of tissue clamp 103 may extend downwardly in a direction that is generally away from the direction in which sides of tissue clamp 103 curve upwardly, so that each leg 104 may contact flange 106 and force sides of tissue clamp 103 upwardly toward saddle 101, thereby securing a conduit between tissue clamp 103 and saddle 101.

FIG. 21 shows a conduit coupling device according to an embodiment of the invention. According to this embodiment of the invention, conduit coupling device comprises a pair of couplers 100 and a clamp 108. Couplers 100 may include complementary mating surfaces 107, 107'. In one embodiment of the invention, conduit coupling device may be used to connect conduits 190, 191 that extend substantially parallel to one another in the same or in a substantially similar plane, as shown in FIG. 21. An incision may be made in each conduit 190, 191, so that a saddle 101 of each coupler 100 may be positioned within a respective conduit 190, 191. Each tissue clamp 103 may be heated to its transition temperature, so that each tissue clamp 103 transforms to its predetermined shape to secure a respective conduit 190, 191 between a respective tissue clamp 103 and saddle 101. Thus, each coupler 100 may be positioned in fluid communication with a respective conduit 190, 191.

Once each coupler 100 is secured to a respective conduit 190, 191, respective flanges 106 and mating surfaces 107, 107' of each coupler 100 may be positioned in alignment, as shown in FIG. 21. A clamping ring 108 may be positioned around a flange 106 of each coupler 100 and couplers 100 may be secured together by crimping clamping ring 108 around flanges 106.

Figure 25:
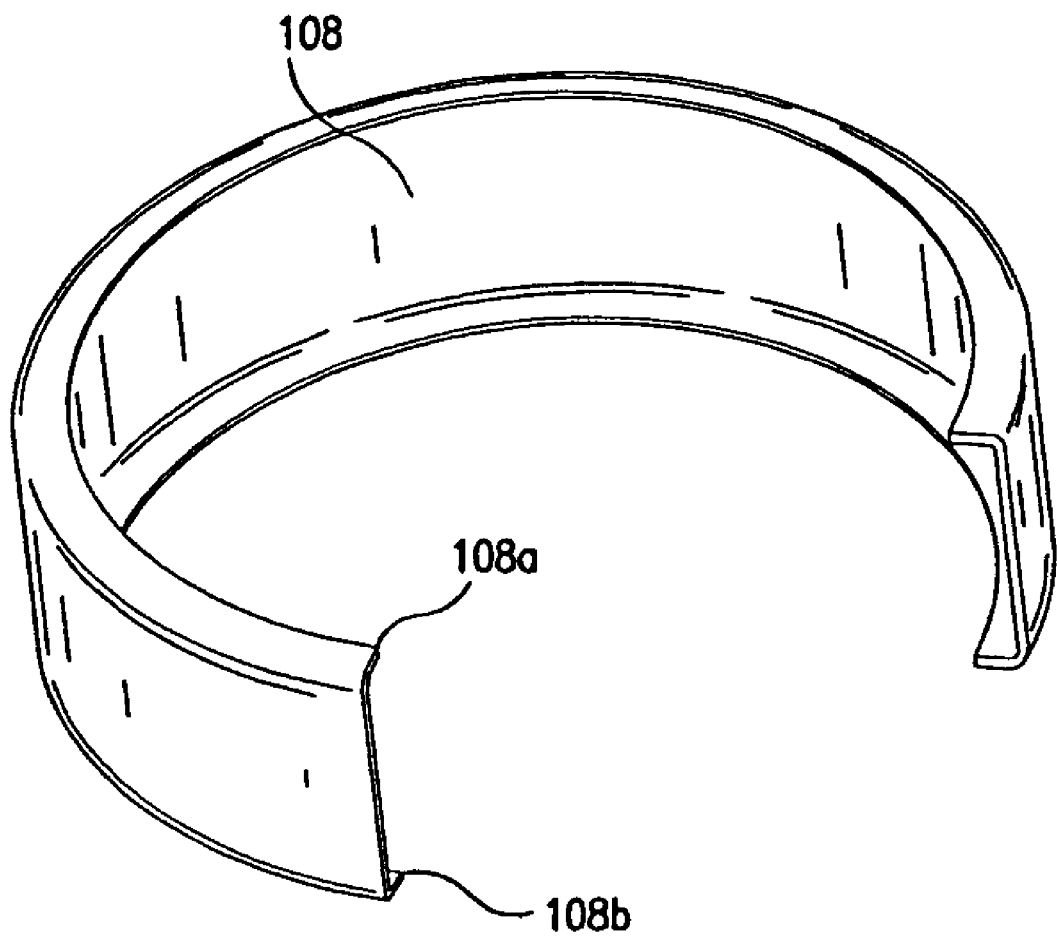
FIG. 25 depicts a clamping ring.

As shown in FIG. 25, clamping ring 108 may be formed with lips 108*a*, 108*b* that may be seated around an edge of each respective flange 106 of coupler 100, thereby securing flanges 106 and respective couplers 100 together. Clamping ring 108 may be made from a metal such as steel, titanium, a nickel titanium alloy, or the like.

In one embodiment of the invention, couplers 100 may be positioned in and secured to respective conduits 190, 191 before flanges 106 of each coupler 100 may be positioned in alignment and secured by clamping ring 108. In another embodiment of the invention, a pair of couplers 100 may be secured together at their respective flanges 106 by application of clamping ring 108 before saddle 101 of each coupler 100 is positioned in and secured to a respective conduit 190, 191. For example, flange 6 of each coupler 100 may be secured by clamping ring 108 before saddle 101 of each coupler 100 is positioned in and secured to each conduit 190, 191. In a further embodiment of the invention, a pair of couplers 100 may be welded, glued, or otherwise joined together at respective flanges 106. In a still further embodiment of the invention, a pair of couplers 100 may be welded, glued, or otherwise joined together, eliminating flanges 106, or a pair of couplers 100 may be manufactured integrally as a single unit.

In still further embodiments of the invention, a conduit coupling device may be manufactured from a pair of couplers 100 that may be positioned at various, predetermined angles and orientations relative to one another, so that the conduit coupling device may be used to connect conduits that may be positioned at various angles and orientations to one another.

Figure 27:
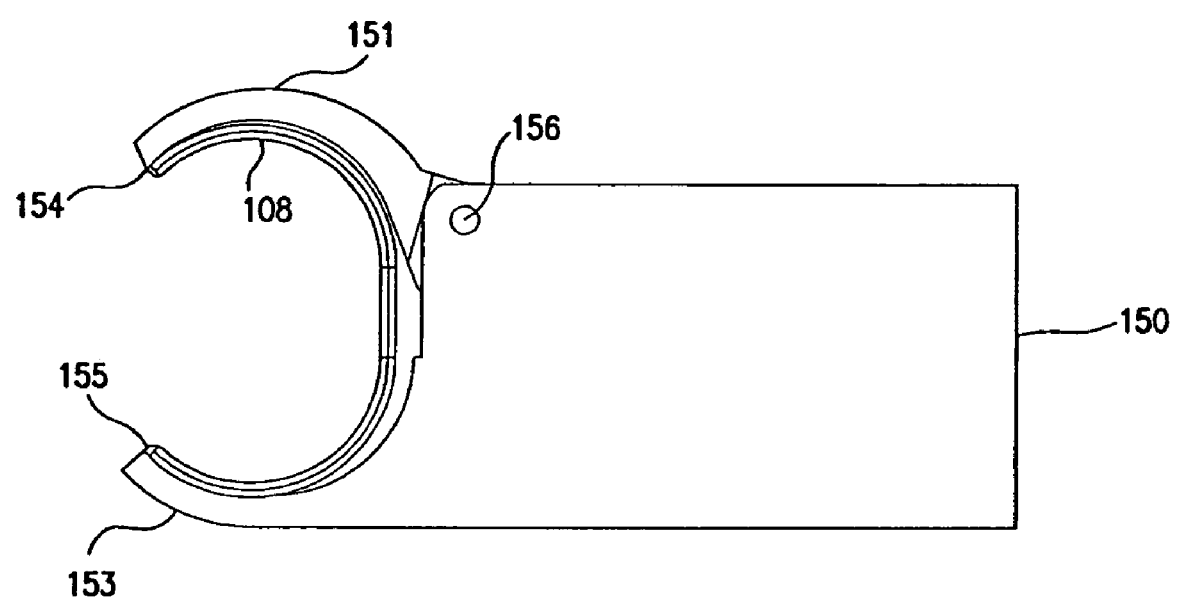
FIG. 27 depicts a ring clamp device for use with the conduit coupling device of the present invention.

Clamping ring 108 may be applied to flanges 106 of each coupler 100 with a ring clamping device 150, shown in FIG. 27. Ring clamping device 150 may include arms 151, 153. A lip 154, 155 may be positioned at a distal end of each arm 151, 153. Clamping ring 108 may be positioned within arms 151, 153 of ring clamping device 150, so that a respective lip 154, 155 of each arm 151, 153 contacts and engages a respective end of clamping ring 108 to retain clamping ring within ring clamping device 150.

Ring clamping device 150 may be actuated, such that arms 151, 153 move outwardly and inwardly relative to one other. In an embodiment of the invention shown in FIG. 28, arm 151 may pivot about a pivot point 156 and move outwardly and inwardly relative to arm 153, which may be secured to or otherwise formed integrally with a body of ring clamping device 150. In another embodiment of the invention (not shown), both arms 151, 153 may pivot about respective pivot points 156 and move outwardly or inwardly relative to one another. In a further embodiment of the invention (not shown), both arms may move in a radial direction relative to the body of ring clamping device 150 and move toward and away from one another.

In each embodiment of the invention, clamping ring 108 may be positioned within ring clamping device 150, such that a lip 154, 155 of each arm 151, 153 contacts a respective end of clamping ring 108. Ring clamping device 150 may be actuated such that arms 151, 153 move away from one another. As arms 151, 153 move away from one another, lips 154, 155 pull each respective end of clamping ring 108 apart, thereby expanding clamping ring 108 outwardly. Ring clamping device 150 may then position clamping ring 108 around flanges 106 of a pair of couplers 100 that may be positioned in alignment. Ring clamping device 150 may be re-actuated, so that arms 151, 153 move toward one another, thereby crimping clamping ring 108 securely around flanges 6 of each coupler 100 to secure couplers 100 together to form a conduit coupling device. As arms 151, 153 move toward one another, lips 154, 155 disengage from respective ends of clamping ring 108 and release clamping ring 152. Once clamping ring 108 has been crimped around flanges 106 of each coupler 100, clamping ring provides a permanent junction retaining each coupler 100 in alignment and position.

In an embodiment of the invention in which couplers 100 may be connected to form a conduit coupling device between conduits of substantially similar cross-sectional area, each coupler 100 may be configured with a channel 102 the cross-sectional area of which is constant or substantially constant. Each coupler 100 may be configured with a cross-sectional area that is the same as or substantially similar to that of another coupler 100 and to the cross-sectional areas of each respective conduit. Thus, a conduit coupling device formed according to this embodiment of the invention may be used to connect two conduits of the same or substantially similar cross-sectional area and to maintain a constant or substantially constant cross-sectional flow area from one conduit to the other conduit. By maintaining the same or a substantially constant cross-sectional flow area, a conduit coupling device according to this embodiment of the invention may reduce or eliminate flow disturbances and velocity or rate changes in fluid flowing from one conduit through conduit coupling device to another conduit, so that the flow of fluid and elements suspended therein, such as blood cells or the like, may not be disrupted unnecessarily. In addition, clotting mechanisms may not be activated as may occur when fluid flow patterns change.

In another embodiment of the invention in which couplers 100 may be connected to form a conduit coupling device between conduits having different cross-sectional areas, each coupler 100 may be configured with a channel 102 the cross-sectional area of which transitions between the different cross-sectional areas of the conduits to be connected. For example, a first coupler 100 may be configured with an elliptical cross-sectional area that is the same as or substantially similar to the cross-sectional area of the conduit in which a saddle 101 of first coupler 100 may be positioned. A second coupler may be designed with an elliptical cross-sectional area that is substantially similar to the cross-sectional area of the second conduit in which a saddle 101 of the second coupler 100 may be positioned. As the channel 102 of each coupler 100 transitions from a substantially elliptical cross-sectional area to a substantially circular cross-sectional area, the cross-sectional area of each channel 102 may increase or decrease, such that the cross-sectional areas of each channel 102 are the same or substantially similar adjacent to flanges 106 of each coupler 100. In this way, conduits of different cross-sectional area may be connected while reducing or eliminating disruptions in the flow of fluid from one conduit to another conduit, via conduit coupling device. Because the cross-sectional configuration of each channel 102 of each coupler 100 may be substantially circular at flange 106, couplers 100 may be rotated relative to one another around their centerline axes 115, so that couplers 100 may be used to connect conduits that may be positioned transversely to one another, as shown, for example, in FIG. 26C.

Coupler 100 may be fabricated from a variety of materials. For example, coupler 10 may be fabricated of a polymer, such as polytetrafluoroethylene, PEEK, polycarbonate, polyurethane, polypropylene, nylon, or the like. An advantage of polymers is that such materials may be relatively inert and therefore less likely to cause clotting in fluid such as blood than other materials. Also, polymers may be fabricated to include additives, such as biochemical agents, that may dissipate over time into surrounding tissues. Additives may include anti-platelet agents, anti-smooth muscle cell growth factors, anti-inflammatory agents, anti-fibrin agents, and anti-thrombin agents. Use of these agents may improve the patency rate of conduit coupling devices placed inside blood vessels by limiting biologic reactions of body tissue and conduits to the implanted devices.

In other embodiments of the invention, couplers may be fabricated of metal, such as stainless steel, nickel titanium alloy, or the like. An advantage of such metals is their higher strength compared to other materials, enabling metal couplers to be fabricated with a wall thickness that is less than a thickness of couplers made of other materials. Metal couplers may have a wall thickness of about $7.87 \times 10^{-5}$ mm (0.002 inches) to about $19.69 \times 10^{-5}$ mm (0.005 inches). Fluid contacting surfaces of metal couplers may be coated with one or more polymers such as silicone or polyurethane to limit the reaction of fluid and tissue to the implant. In turn, these coatings may include biochemical agents described above that may improve the biocompatibility of couplers with conduits and other body tissue.

In a preferred embodiment, tissue clamps 3 may be made of nitinol. Moreover, suitable nitinol may be heat treated, such that its austenitic transition temperature is well below room temperature, for example, at about 10° C., and such nitinol may be in its superelastic state at room temperature. Consequently, tissue clamps 103 made from such nitinol may be inserted into a holder and delivery device 160, as described below with respect to FIGS. 31-34, by simply bending the nitinol tissue clamps into position. When such tissue clamps are released by device 160 at a temperature above room temperature, such tissue clamps spring into their original (pre-bent) shape.

In operation, a coupler 100 may be positioned in a conduit 190 by making an incision at a desired location. The length of the incision preferably is less than the longest axial dimension of saddle 101. Saddle 1 then may be inserted through the incision into conduit 190. Conduit 190 stretches slightly over edges of saddle 101. The curvature of saddle 101 is adapted to match the inside radius of conduit 190, so that conduit 190 may not be distorted by saddle 101. Saddle 101 may be configured with different radii of curvature to fit conduits of different inner radii. Tissue clamp 103 remains outside conduit 190.

Once coupler 100 is positioned inside conduit 190, tissue clamp 103 may be heated to its transition temperature using a warm solution, e.g., a sterile saline solution. The transition temperature preferably is a temperature that is at or above a human body temperature. When tissue clamp 103 is heated to its transition temperature, tissue clamp 103 returns to a predetermined shape, which may be a shape as shown in FIGS. 20 and 29, that secures conduit 190 between tissue clamp 103 and saddle 101. If tissue clamp 103 is made of nitinol, once coupler 100 is positioned inside conduit 190, tissue clamp 103 may be released as its transition temperature is at about 10° C., a temperature that is well below, for example, human body temperature. When nitinol tissue clamp 103 is released, tissue clamp 103 returns to a predetermined shape, which may be the shape as shown in FIGS. 20 and 29, that secures conduit 190 between tissue clamp 103 and saddle 101. Dimples 105 or teeth 109, or both, may be formed on tissue clamp 103 to enhance the contact between tissue clamp 103 and conduit 190. Two conduits may be connected by placing a coupler 100 within each conduit and connecting the couplers 100 at their respective flanges 106 to form a conduit coupling device, as shown for example in FIG. 21.

Figure 26A:
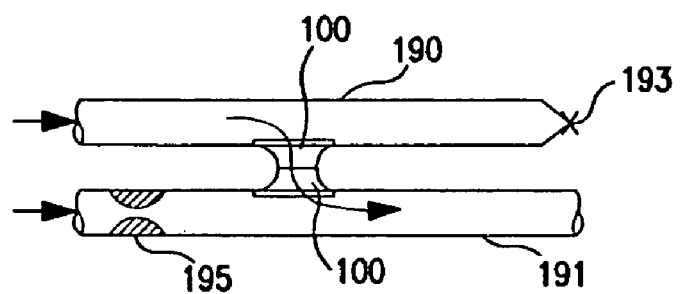
FIGS. 26A-26D depict anastomotic applications of the conduit coupling device with conduits of varying condition.

As shown in FIGS. 26A-26D, a conduit coupling device formed from a pair of couplers 100 may be used to form various connections between conduits. As shown in FIG. 26A, a side-to-side connection or anastomosis may be formed by connecting a first conduit 190 to a second conduit 191 to bypass a blockage 195 in second conduit 191. A coupler 100 may be positioned in, and secured to, a respective conduit 190, 191. A flange 106 of each coupler 100 may be aligned and secured by a clamping ring 108 (not shown). A distal end of first conduit 190 may be closed using a fastener 193, such as a clip, suture, clamp or the like, to prevent flow of fluid through distal end. As illustrated by arrows in FIG. 26A, fluid may flow from first conduit 190, through couplers 100 to a distal end of second conduit 191, thereby bypassing blockage 195.

Figure 26B:
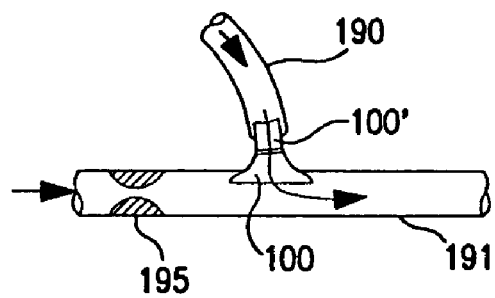

In another embodiment of the invention, couplers 100 may be configured to form a conduit coupling device that connects conduits that may be transverse to one another, as shown in FIG. 26B. This embodiment enables couplers to form a conduit coupling device that connects blood vessels that may lie at varying angles to one another in the body. For example, an end-to-side anastomotic connection may be made by placing a first coupler 100' in a distal end of a first conduit 190 and a second coupler 100 in a second conduit 191 to form a conduit coupling device that bypasses a blockage 195 in second conduit 191. In this embodiment, first coupler 100' may be placed in a distal end of first conduit 190 and may include a saddle 101, a channel 102, and a tissue clamp 103 of different configuration than those disclosed in previously-described embodiments of the invention. For example, saddle 101' and channel 102' of first coupler 100' may have a substantially circular cross-sectional throughout their respective lengths, and tissue clamp 103 may have a substantially circular cross-sectional that conforms to the shape of saddle 101'. Tissue clamp 103' may include dimpled holes 105, teeth 109, or both, to improve the connection between tissue clamp 103' and first conduit 100 and to secure first conduit 100 between saddle 101' and tissue clamp 103'. A second coupler 100 may be positioned in and secured to second conduit 109. First coupler 100' and second coupler 100 may be secured together to form a conduit coupling device that establishes fluid communication between first conduit 190 and second conduit 191, so that fluid may flow therebetween and bypass blockage 195, as illustrated by arrows in FIG. 26B.

Figure 26C:
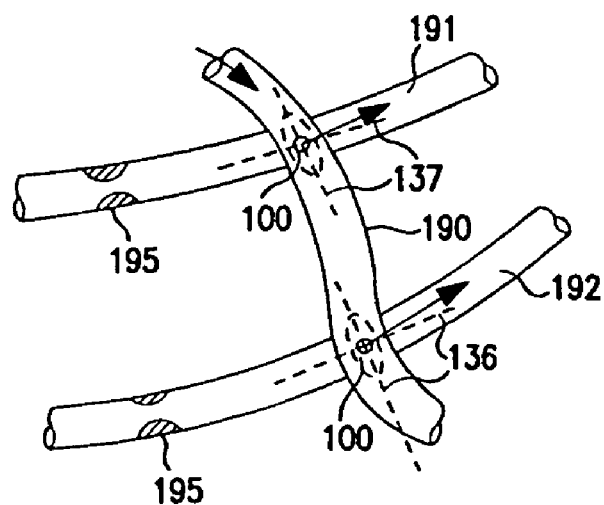

In a further embodiment of the invention, couplers may be configured to form multiple conduit coupling devices and multiple connections between conduits, as shown in FIG. 26C. In this embodiment, a single conduit 190 may be used to supply fluid to two or more blocked conduits 191, 192. The conduit 190 may be positioned transverse to each blocked conduit 191, 192. A pair of couplers 100 may be used to form a conduit coupling device that establishes a connection between single conduit 190 and each respective blocked conduit 191, 192. A coupler 100 of each conduit coupling device is shown in broken lines in FIG. 26C. Because single conduit 190 may be positioned transversely to each blocked conduit 191, 192, conduit coupling devices according to this embodiment of the invention is adopted to conform to and maintain varying angles 120, 121 between single conduit 190 and each blocked conduit 191, 192. Each coupler 100 may be rotated relative to the other coupler of a pair of couplers that form a conduit coupling device to ensure that each saddle 101 of a respective coupler is oriented within a respective conduit 191, 192 to reduce or eliminate tension between single conduit 190 and blocked conduits 191, 192. The circular cross-section of each channel 102 adjacent to flange 106 of each coupler 100 permits rotation of one coupler 100 relative to the other coupler 100 without disrupting the flow path between couplers 100 of a conduit coupling device. By connecting single conduit 190 to each blocked conduit 191, 192, fluid flow may be restored to each blocked conduit 191, 192 at locations distal to blockages 195 in each blocked conduit 191, 192.

Figure 26D:
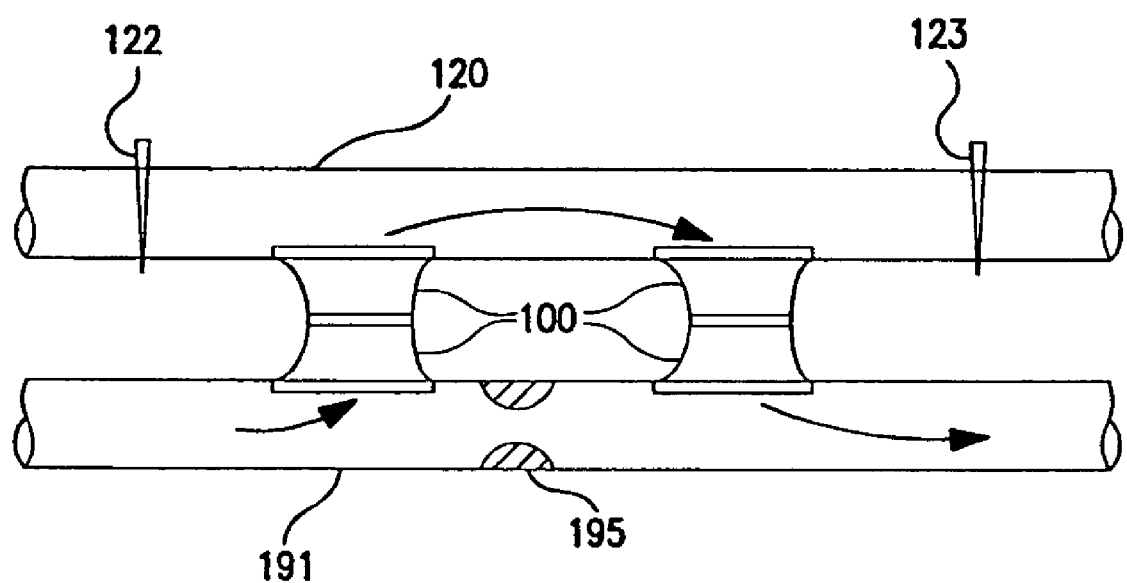

In a still further embodiment of the invention, couplers 100 may be configured to form a pair of conduit coupling devices, as shown in FIG. 26D, so that an adjacent conduit 190 may be used to bypass a blocked conduit 191. A first coupler 100 of each conduit coupling device may be positioned in blocked conduit 191 proximal to, and on either side of, obstruction 195 in conduit 191. A second coupler 100 of each conduit coupling device may be positioned in adjacent conduit 190. First couplers 100 may be connected to respective second couplers 100 to form conduit coupling devices that allow fluid to flow through adjacent conduit 190 and bypass obstruction 195. Conduit 190 may be clipped at positions 122, 123, so that adjacent conduit 190 may serve as a short conduit for fluid to bypass obstruction 195. In this embodiment of the invention, adjacent conduit 190 may comprise a vein, while blocked conduit 191 may comprise an artery.

Figure 30:
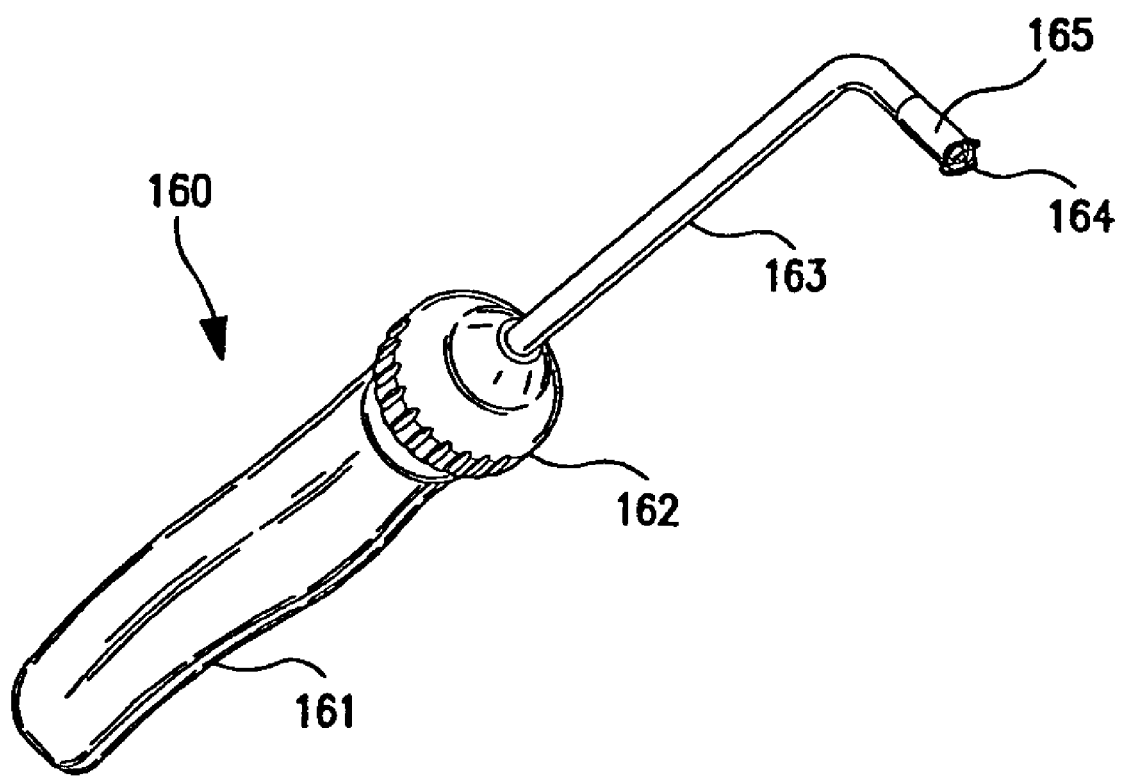
FIG. 30 depicts the connector holding device.

In FIG. 30, an embodiment of holder and delivery device 160, as discussed above, is depicted. Device 160 is used to hold coupler 100 of FIGS. 17-20 with tissue clamp 103 pulled up, e.g., away from, flange 106 and mating surfaces 107, 107′, while coupler 100 is being placed into the blood vessel. In this manner, device 160 prevents tissue clamp 103 from interfering with the placement of coupler 100. Device 160 comprises a handle 161 for grasping device 160 and a rotation knob 162 connecting a holding tube 163 having a flared end 165 to handle 161, whereby coupler 100 may be rotated into position for placement in a blood vessel. Thus, in accordance with FIGS. 31A and 31B, when rotation knob 162 is rotated in the direction of arrow D, coupler 100 and flared end 165 rotate in the direction of arrow E. An inner shaft 164 passes through tube 163 and is separate from and may move independently from tube 163.

Figure 31:
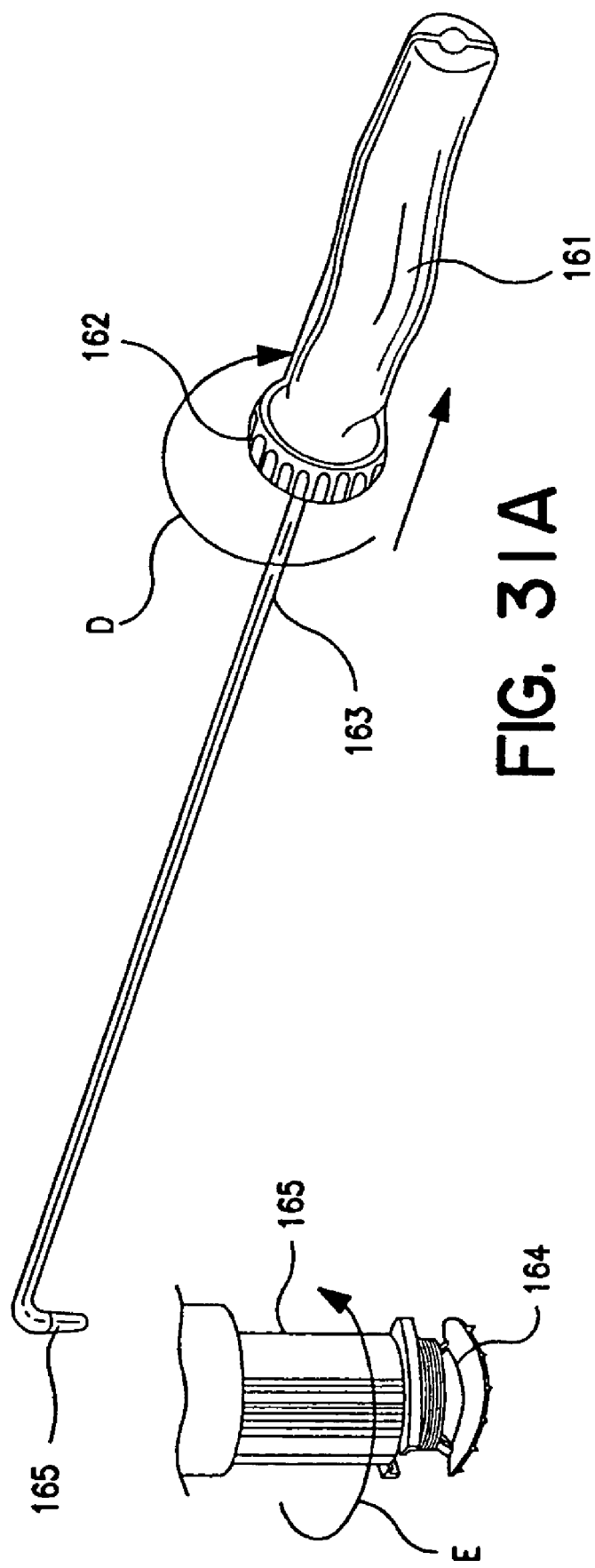
FIG. 31A depicts an embodiment of a coupler holder and delivery device.
FIG. 31B depicts an enlarged view of the tip of the coupler holder and delivery device of FIG. 31A.
Figure 32:
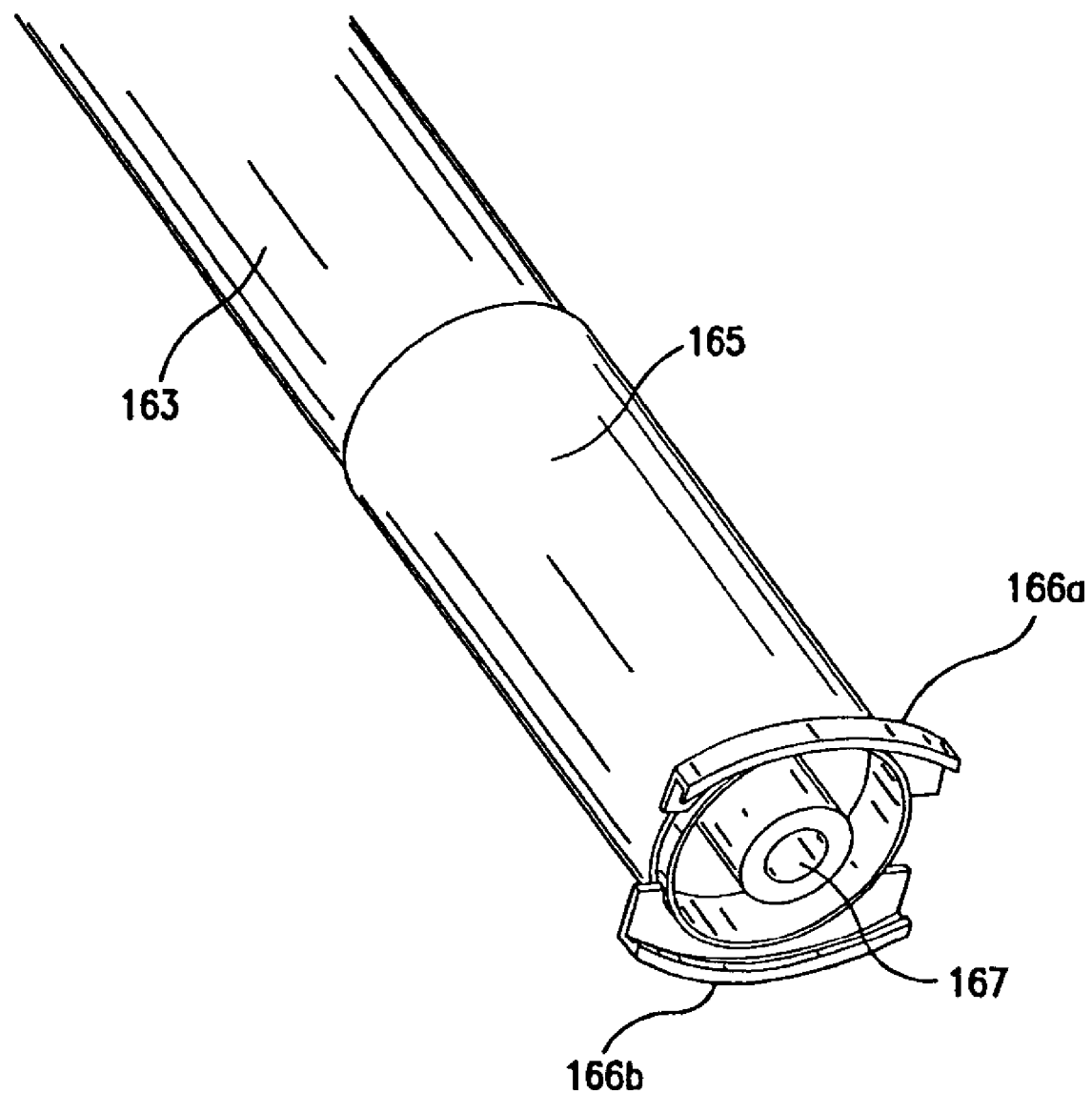
FIG. 32 depicts a distal end of coupler holder and delivery device of FIG. 31.
Figure 33:
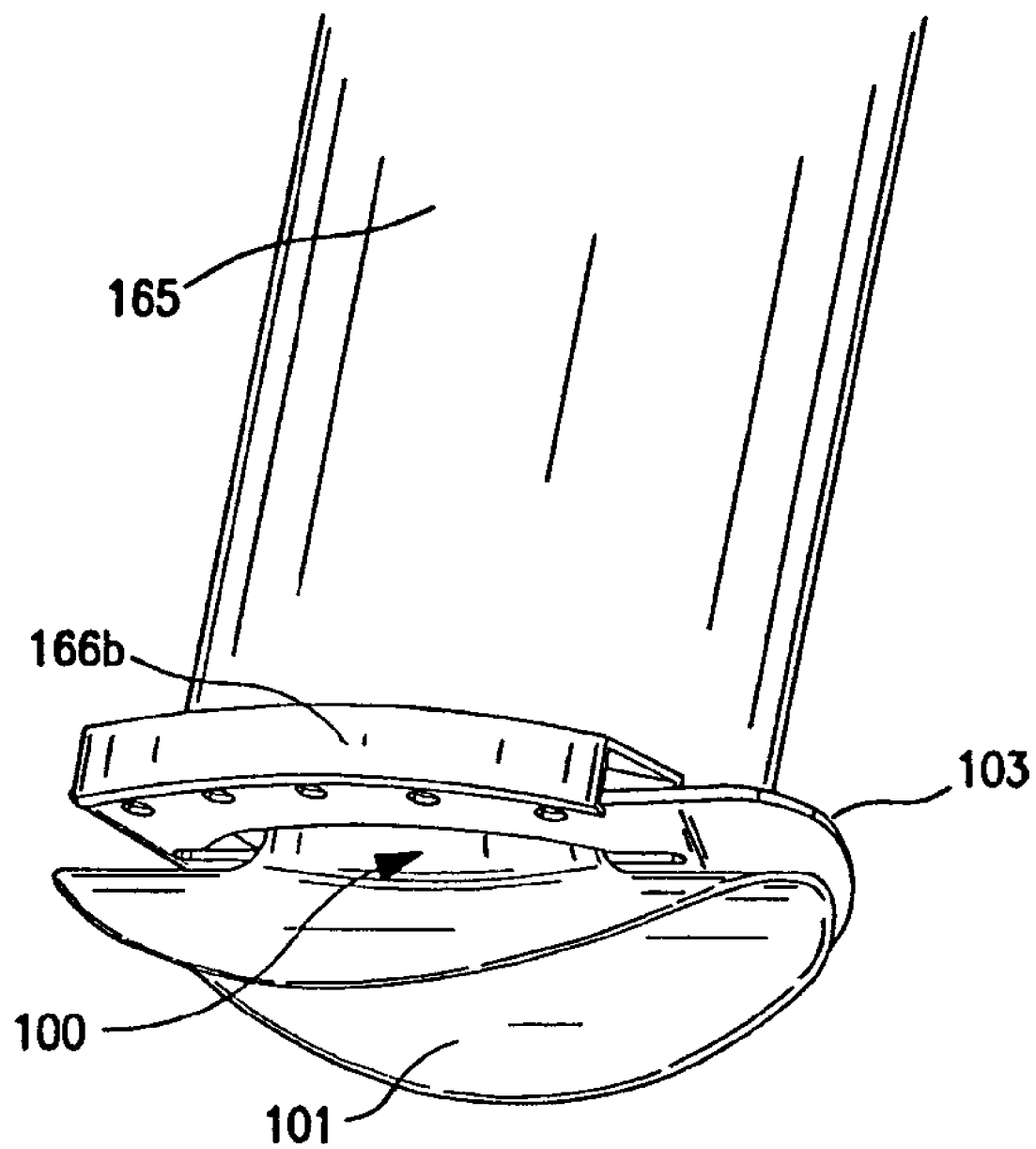
FIG. 33 depicts the coupler held in position prior to delivery to a conduit by coupler holder and delivery device of FIG. 31A.

FIG. 32 depicts flared end 165 of device 160 of FIG. 31. Shaft 164 ends in a conforming end 167, which is adapted to be received in channel 102 of coupler 100. The distal end of tube 163 has opposing, clamp receiving flanges 166a and 166b. When in use, coupler 100 is inserted into flared end 165 of device 160. Tissue clamp 103 is bent and held up and out of the way of saddle 101 of coupler 100 and the distal surface of device 160 by engagement with flanges 166a and 166b of device 160. Referring to FIG. 33, coupler 100 thus is held in position prior to delivery to a blood vessel by device 160 of FIG. 31.

Figure 34:
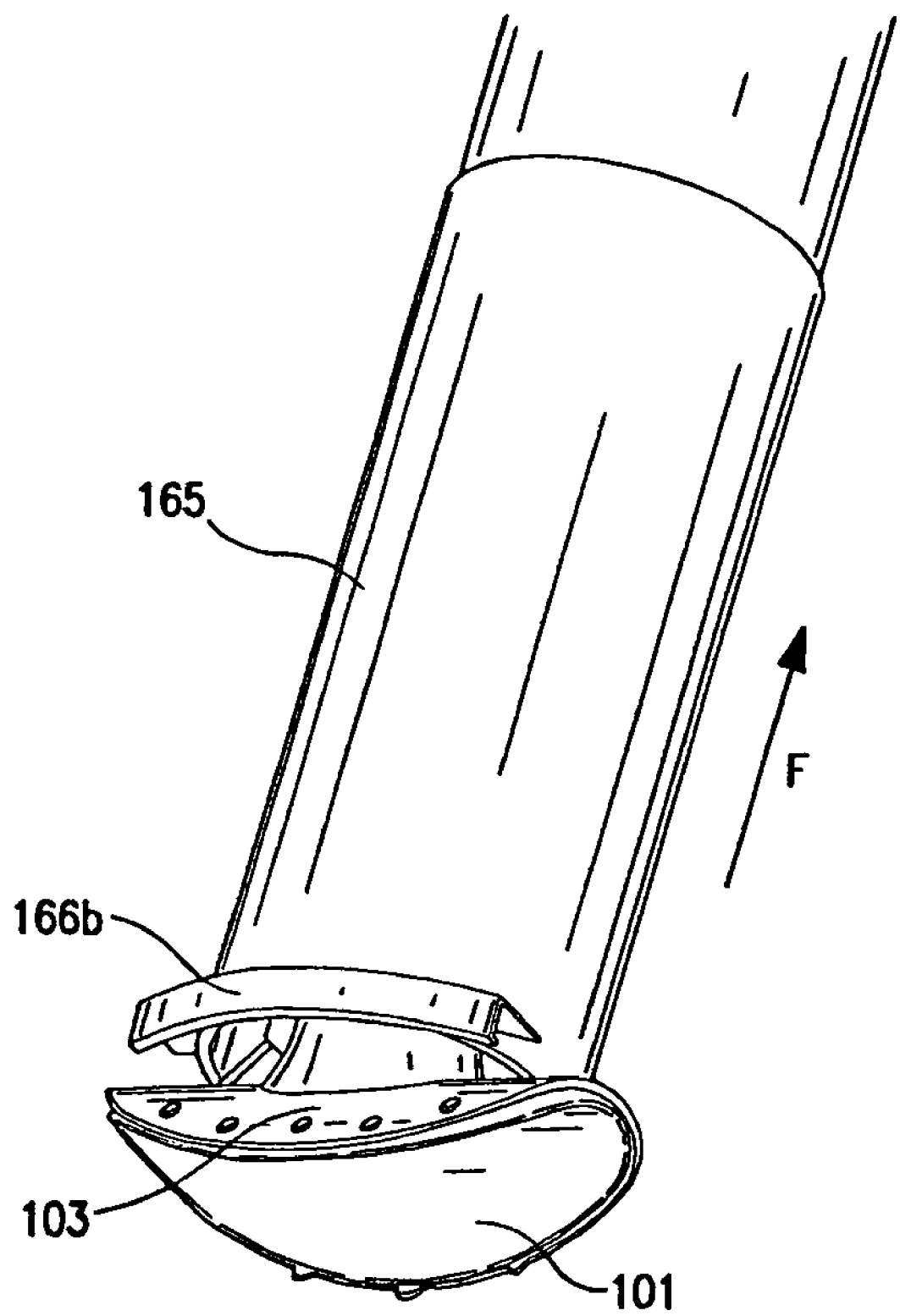
FIG. 34 depicts the coupler immediately after release from the coupler holder and delivery device of FIG. 31A into its final position in the conduit.

FIG. 34 depicts coupler 100 immediately after its release from device 160 of FIG. 31 for placement into position in a blood vessel (not shown). Once coupler 100 is placed into the designated blood vessel, flared end 165 is pulled back in the direction of arrow F, as shown in FIG. 34. As flared end 165 is drawn away from coupler 100, opposing, clamp receiving flanges 166a and 166b also are drawn away from coupler 100. As opposing, clamp receiving flanges 166a and 166b are drawn away from coupler 100, tissue clamps 103 slip from the grasp of flanges 166a and 166b and may snap onto the outer surface of the designated blood vessel (not shown). Thus, tissue clamps 103, e.g., tissue clamps 103 made from nitinol, may resume their pre-bent form and cover the suture attachment of saddle 101 of coupler 100 to the designated blood vessel.

A further advantage of this design is that the heart is often cooled below room temperature during surgery to limit tissue damage during low or no flow conditions. If the tissue is cool, it then may be difficult to warm the tissue clamp to cause it to change shape.

Figure 35A:
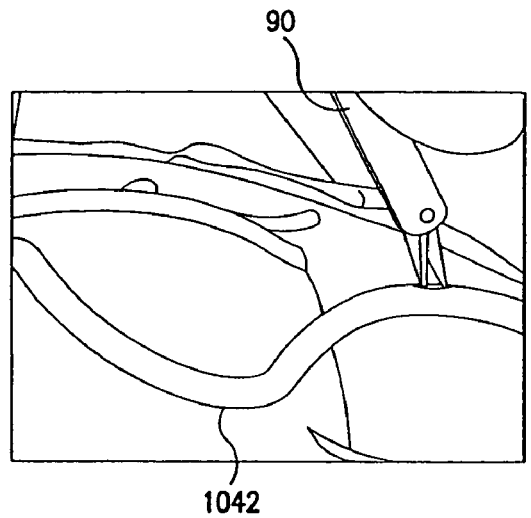
FIGS. 35A-35D depicts a sequence of steps in the placement of the vessel connector in one vessel.
Figure 35B:
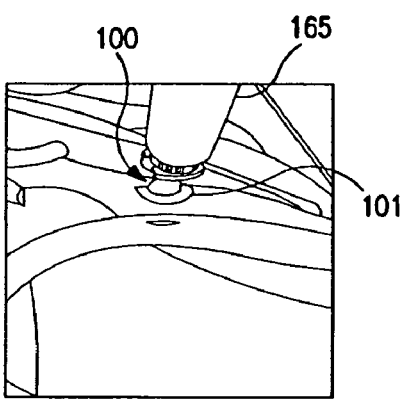
Figure 35C:
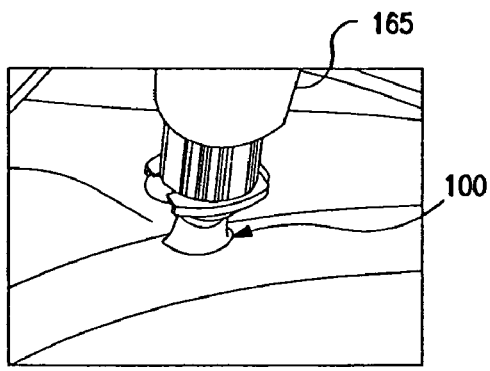
Figure 35D:
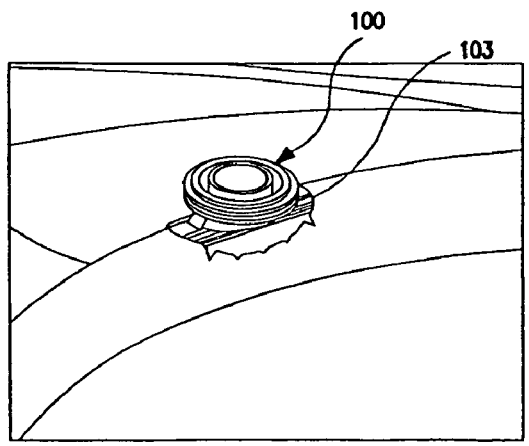

First coupler 100 may be applied to a vessel, as shown in the sequence of images depicted in FIGS. 35A-35D. In FIG. 35A, the surgeon makes an incision into the vessel with scissors 90. In FIGS. 35B and 35C, saddle 101 of first coupler 100 is positioned at the incision and then pushed into the vessel using holder and delivery device 160. As described above with respect to FIG. 34, first coupler 100 is released from flared end 165 of holder and delivery device 160 is drawn back from first coupler 100. Finally, as shown in FIG. 35D, after its release from flared end 165 of holder and delivery device 160, tissue clamp 103 clamps onto the vessel and seals first coupler 100 into the incision. Thus, this seal may be achieved without suturing.

Figure 36B:
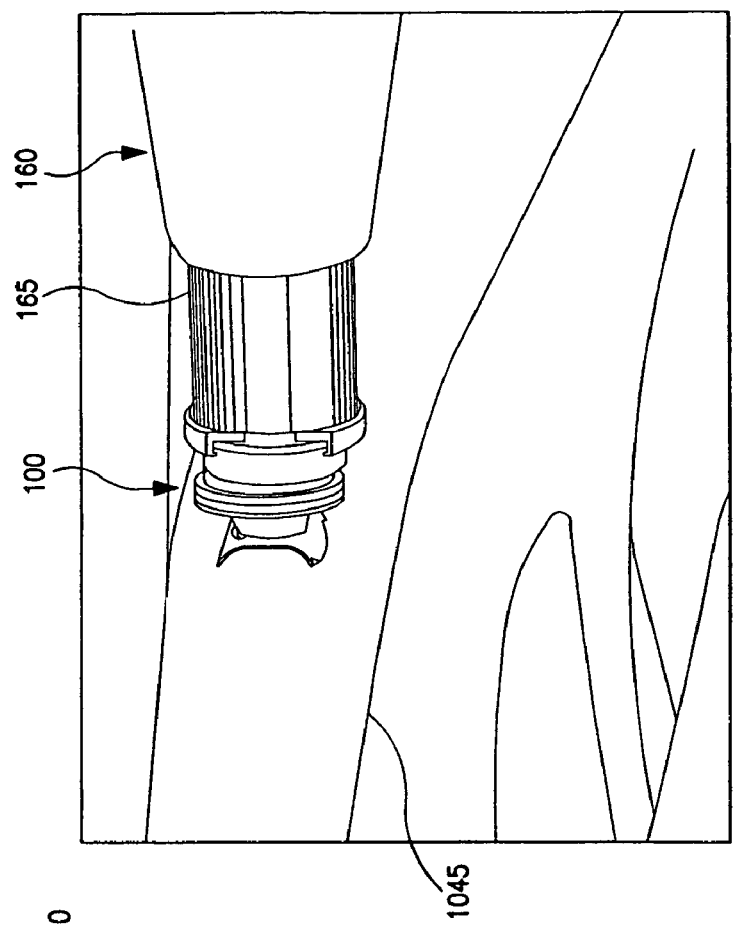
FIGS. 36A and 36B depict a sequence of steps in the placement of the vessel connector in a second vessel.
Figure 36A:
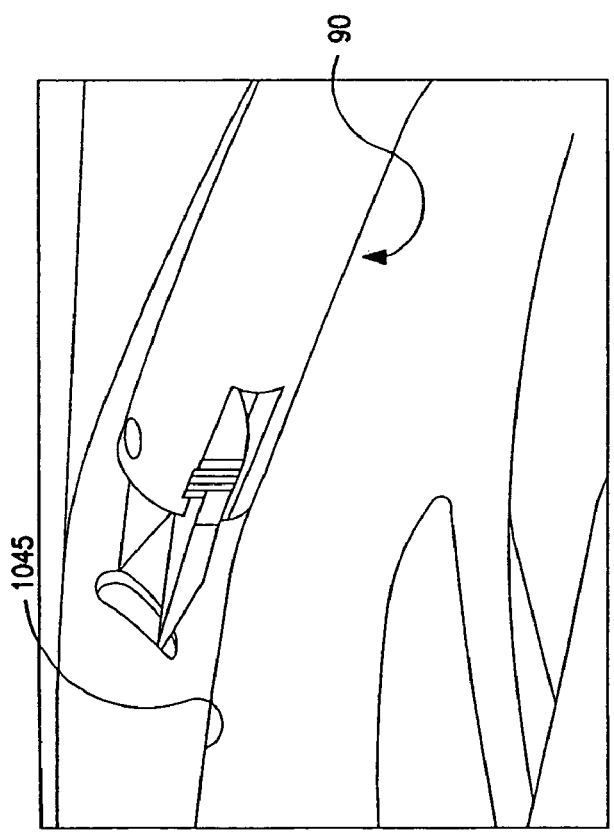

In the sequence of FIGS. 35A-35D, first coupler 100 has been inserted into a coronary vessel 1042. Following the insertion of first coupler 100 into coronary vessel 1042, a second or mating coupler 100 may be inserted into branch vessel 1045 of IMA 1040, as shown in the sequence of FIGS. 36A and 36B. The order of placement of first and second couplers 100 is left to the judgment of the surgeon, for example, it might be desirable to the order described above and to place first coupler 100 into branch vessel 1045 of IMA 1040, followed by placement of second coupler 100 into coronary vessel 1042.

Figure 37:
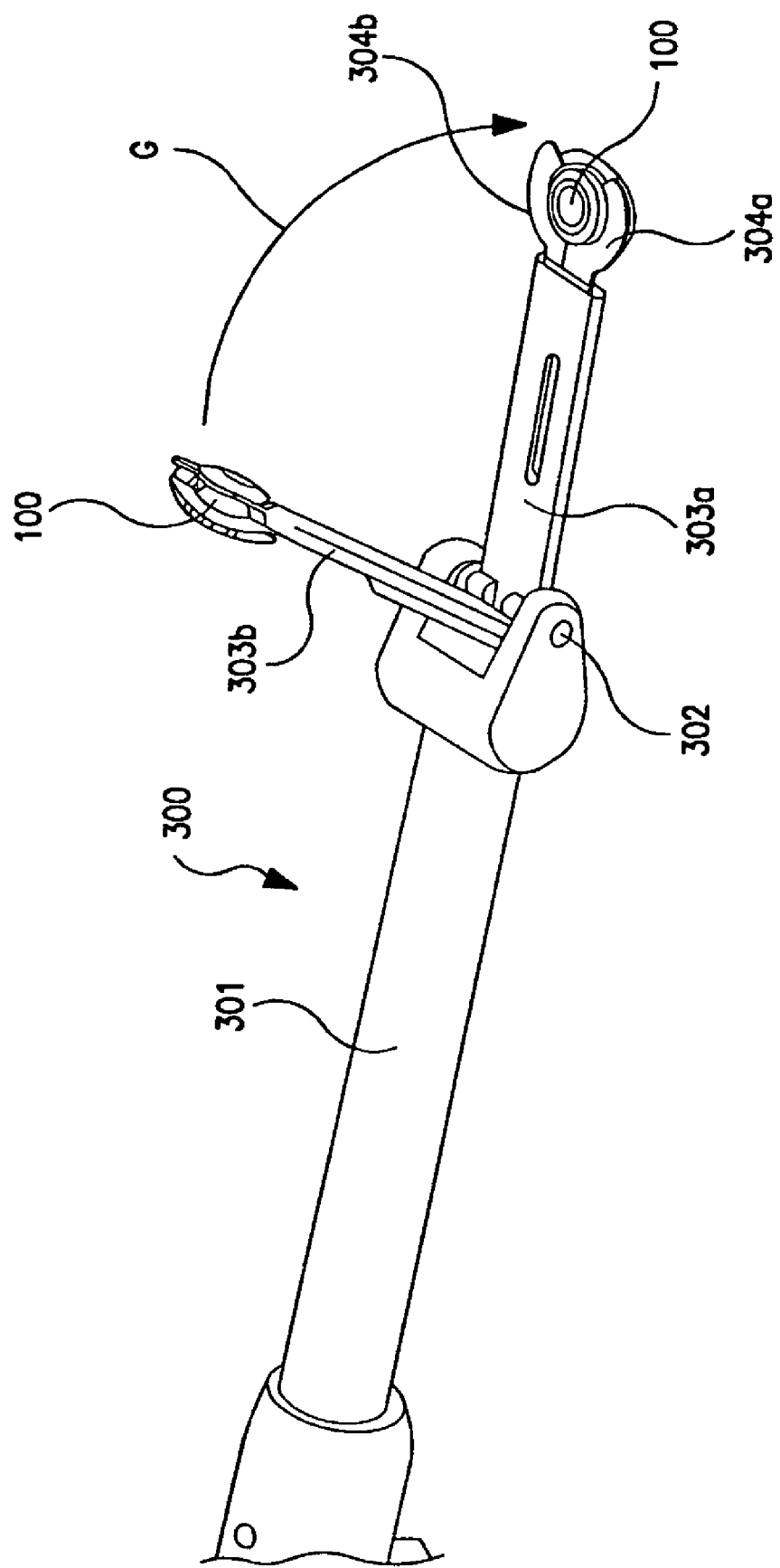
FIG. 37 depicts the device used to connect the vessel connectors.

Referring to FIG. 37, a coupler connection device 300 is shown which may be used to join two coupler 100 together and thereby to couple two vessels. Coupler connection device 300 comprises a connection shaft 301, a pair of coupler connecting arms 303a and 303b, and a connecting pivot 302 by which coupler connecting arms 303a and 303b are brought together. Coupler connection device 300 is guided into the patient's chest cavity by means of connection shaft 300 and mechanical, electrical, or electromagnetic signals, or the like, may be transmitted through connection shaft 300 to actuate one, either, or both of coupler connecting arms 303a and 303b to connect couplers 100. More specifically, each of coupler connecting arms 303a and 303b may be pivotably attached to connecting pivot 302, and arched fingers 304a and 304b may be formed at the distal end of each of coupler connecting arms 303a and 303b. Arched fingers 304a and 304b are shaped to grasp couplers 100. Moreover, mechanical, electrical, or electromagnetic signals, or the like, may be transmitted through connection shaft 300 and through coupler connecting arms 303a and 303b to actuate arched fingers 304a and 304b to grasp or release couplers 100. Thus, for example, once arched fingers 304a and 304b on each coupler connecting arms 303a and 303b have grasped first and second couplers 100, respectively, coupler connecting arm 303a may be held stationary and coupler connecting arm 303b may be actuated to swing in the direction of arrow G to connect first coupler 100 with second coupler 100.

Figure 38A:
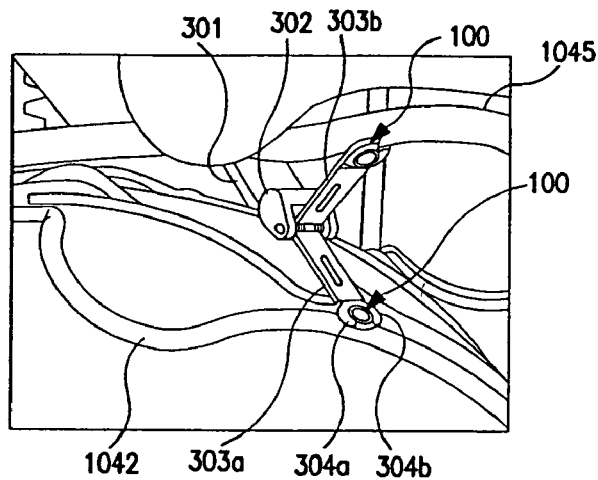
FIGS. 38A-38C depict a sequence of steps in the connecting of the two vessels.
Figure 38B:
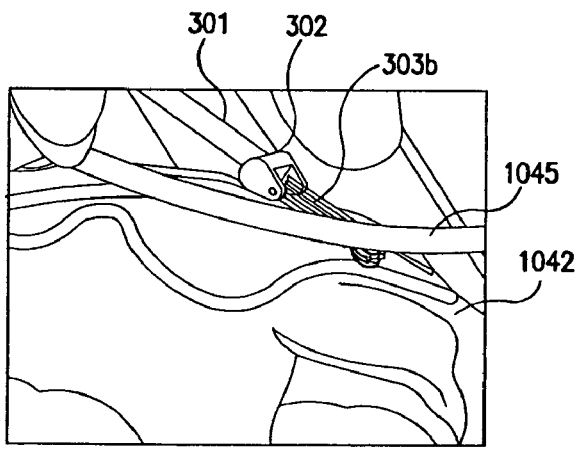
Figure 38C:
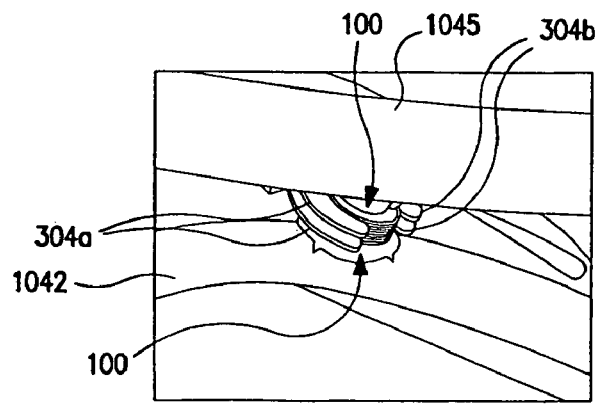

FIG. 38 depicts a sequence of steps for using coupler connection device 300 to connect two vessels, such as those described with respect to FIGS. 35A-35D, 36A, and 36B, with first and second couplers 100. In FIG. 38A, coupler connection device 300 has been inserted in to the patient's chest cavity and arched fingers 304a and 304b on coupler connecting arm 303a have grasped first coupler 100 in coronary vessel 1042 and arched fingers 304a and 304b on coupler connoting arm 303b have grasped second coupler 100 in branch vessel 1045 of IMA 1040. Referring to FIG. 38B, once coupler connecting arms 303a and 303b have grasped first and second couplers 100, respectively, coupler connecting arm 303a may be held stationary and coupler connecting arm 303b may be actuated to swing toward coupler connecting arm 303a to connect first coupler 100 with second coupler 100. Finally in FIG. 38C, first and second couplers 100 are joined together. Arched fingers 304a and 304b on each of coupler connecting arms 303a and 303b then may be actuated to release first and second couplers 100, so that coupler connection device 300 may be removed form the patient's chest cavity.

Figure 39B:
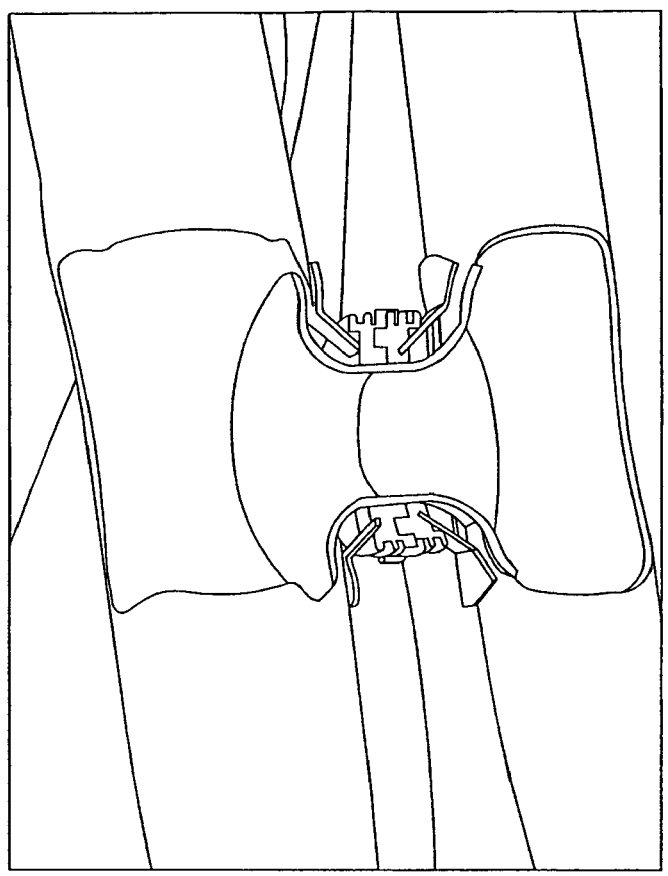
FIG. 39B depicts a cross-sectional view of the final connected vessels.
Figure 39A:
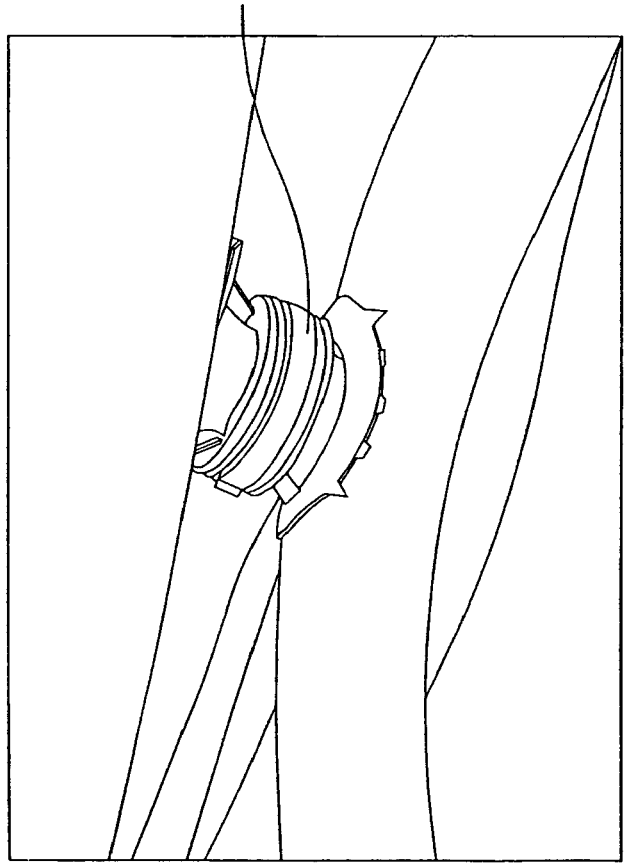
FIG. 39A depicts an external view of the final connected vessels.
Figure 40:
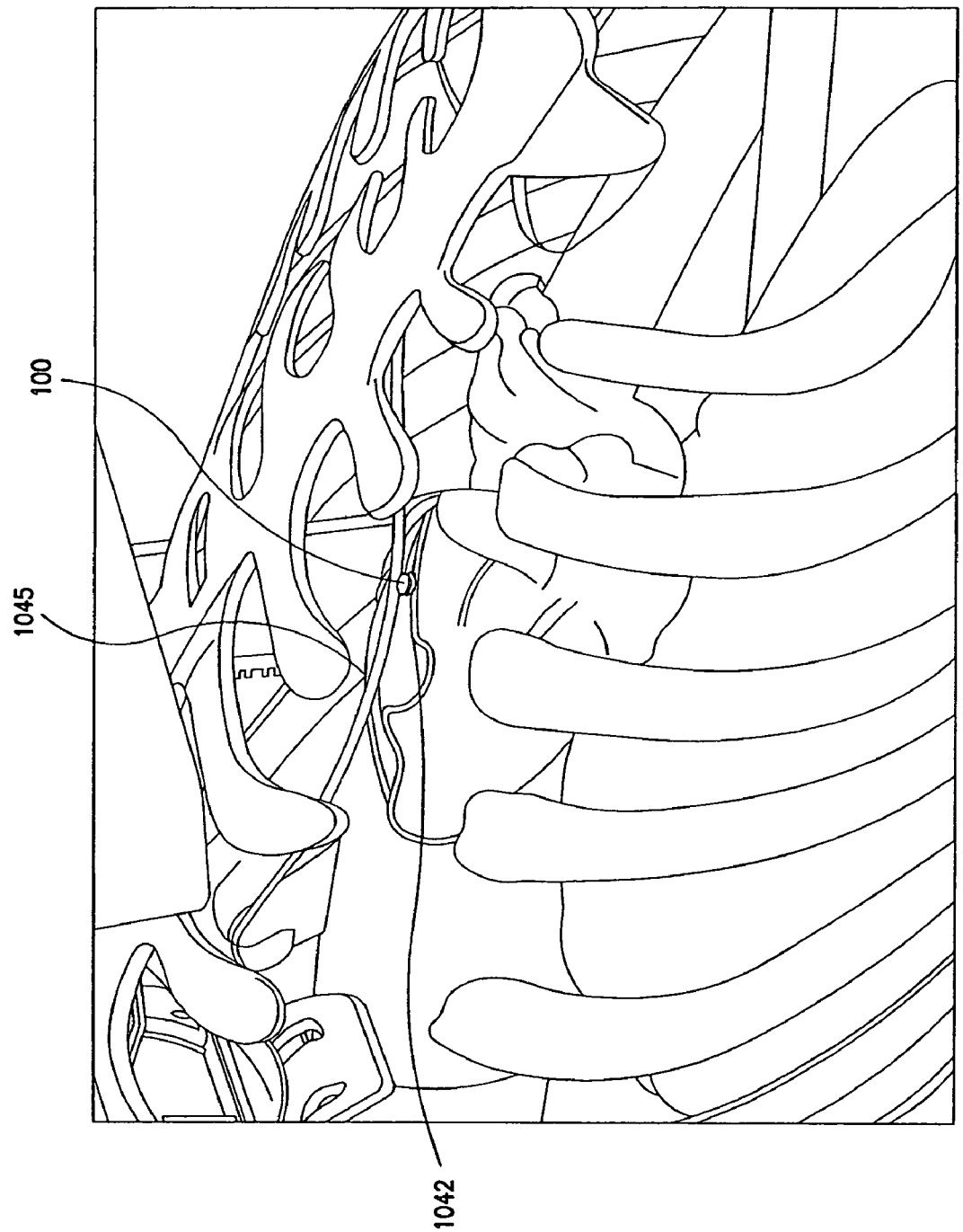
FIG. 40 depicts the final vessel connection in the body.

FIG. 39A depicts an external view of the final connected vessels, e.g., coronary vessel 1042 and branch vessel 1045 of IMA 1040, and FIG. 39B depicts a cross-sectional view of the final connected vessels. Couplers 100 have been secured with clamping ring 108 and have created and alternate flow path for blood around a damaged section of the vessel without the necessity of suturing the connections in place. FIG. 40 depicts the placement of couplers 100 with respect to fulcrum device 14 and incision 1020 in the patient's chest.

Exit

FIG. 41 shows the final result on the patient. The incision is closed and leaves a small wound 1020' on the patient.

While the invention has been described in connection with preferred embodiments, it will be understood by those of ordinary skill in the art that other variations and modifications of the preferred embodiments described above may be made without departing from the scope of the invention. Moreover, other embodiments of the present invention will be apparent to those of ordinary skill in the art from a consideration of the specification or a practice of the invention disclosed herein, or both.

We claim:

1. A coupler comprising:
   a saddle having a longitudinal axis extending along a first direction;
   a channel extending from a first end to a second end along a second direction substantially perpendicular to the first direction, said first end having a substantially elliptical cross-section of a first width in the first direction connected to said saddle and said second end having a substantially circular cross-section of a second width in the first direction;
   a tissue clamp positioned around said channel, said tissue clamp comprising:
      a base portion;
      a clamping portion extending from said base portion, said clamping portion configured to elastically move from a clamped position substantially corresponding to a shape of said saddle to an unclamped position not corresponding to the shape of said saddle; and
      a connection portion configured to connect said clamping portion to said channel and limit the axial position of said clamping portion in the unclamped position relative to said saddle; and
   a flange formed substantially at said second end of said channel,
   wherein the first width of the substantially elliptical cross-section is greater than the second width of the substantially circular cross-section,
   wherein said connection portion comprises a pair of legs, which extend and position said tissue clamp adjacent to said saddle when said tissue clamp is heated to a transition temperature,
   wherein said pair of legs are connected to said channel at said flange formed substantially at said second end of said channel, and
   wherein said pair of legs are configured to bias said clamping portion towards said saddle in the clamped position.

2. The coupler of claim 1, wherein said tissue clamp comprises a shape-memory alloy.

3. The coupler of claim 2, wherein said shape-memory alloy comprises a nickel titanium alloy.

4. The coupler of claim 1, wherein said tissue clamp comprises a plurality of teeth positioned along a periphery of said tissue clamp.

5. The coupler of claim 1, wherein said tissue clamp comprises a plurality of dimpled holes formed therethrough.

6. The coupler of claim 1, wherein a cross-sectional area of said channel remains substantially constant as said channel transitions from said first end to said second end.

7. The coupler of claim 1, wherein a cross-sectional area of said channel increases or decreases as said channel transitions from said first end to said second end.

8. The coupler of claim 1, further comprising a mating surface formed adjacent to said flange.

9. The coupler of claim 1, wherein said tissue clamp is made from a material having an austenitic transition temperature less than about 10° C.

10. The coupler of claim 1, wherein said tissue clamp is made from a material having an austenitic transition temperature about equal to or slightly greater than body temperature.

11. The coupler of claim 9, wherein said material is nitinol.

12. The coupler of claim 1, wherein said saddle has a predetermined shape that is rigid at a temperature of a range from 15° C. to 43° C.

13. The coupler of claim 12, wherein said saddle has a predetermined shape that is rigid at a temperature of about 38° C.

* * * * *